United States Patent [19]

Petrzilka

[11] Patent Number: 4,528,114
[45] Date of Patent: Jul. 9, 1985

[54] ACETYLENES

[75] Inventor: Martin Petrzilka, Kaiseraugst, Switzerland

[73] Assignee: Hoffmann-La Roche Inc., Nutley, N.J.

[21] Appl. No.: 446,835

[22] Filed: Dec. 3, 1982

[30] Foreign Application Priority Data

Dec. 18, 1981 [CH] Switzerland .................. 8111/81
Sep. 23, 1982 [CH] Switzerland .................. 5623/82

[51] Int. Cl.³ .................. C07C 13/28; C07C 15/50; C07C 43/21; C07C 69/75; C07C 121/70; C07C 5/00; C07C 25/24; C07C 67/08; C07D 319/06; C07D 239/26; C07D 239/27; C07D 239/28; G02F 1/13; C09K 3/34

[52] U.S. Cl. .................. 252/299.6; 252/299.5; 252/299.61; 252/299.62; 252/299.63; 252/299.64; 252/299.65; 252/299.66; 252/299.67; 260/464; 260/465 D; 260/465 F; 260/465 K; 350/350 R; 350/350 S; 544/242; 544/298; 549/369; 549/373; 560/1; 560/61; 560/72; 560/73; 560/104; 560/106; 568/631; 568/635; 568/642; 585/20; 585/25

[58] Field of Search .................. 252/299.61, 299.62, 252/299.6, 299.63, 299.64, 299.65, 299.66, 299.67, 299.5; 260/464, 465 D, 465 F, 465 K; 544/298, 242; 549/373, 369; 585/20, 25; 568/631, 635, 642; 560/1, 61, 72, 73, 104, 106; 350/350 R, 350 S

[56] References Cited

U.S. PATENT DOCUMENTS

| | | | |
|---|---|---|---|
| 3,923,857 | 12/1975 | Boller et al. | 260/465 D |
| 3,987,116 | 10/1976 | Diamond | 260/649 R |
| 3,997,536 | 12/1976 | Boller et al. | 252/299.61 |
| 4,001,137 | 1/1977 | Steinstrasser | 252/299.64 |
| 4,016,214 | 4/1977 | Douglas et al. | 260/649 F |
| 4,062,798 | 12/1977 | Boller et al. | 252/299.61 |
| 4,130,502 | 12/1978 | Eidenschink et al. | 252/299.63 |
| 4,181,625 | 1/1980 | Eidenschink et al. | 252/299.63 |
| 4,219,256 | 8/1980 | Gray et al. | 252/299.62 |
| 4,261,651 | 4/1981 | Gray et al. | 252/299.63 |
| 4,263,457 | 4/1981 | Takeda et al. | 260/465 G |
| 4,273,929 | 6/1981 | Boller et al. | 252/299.61 |
| 4,298,528 | 11/1981 | Sethofer | 252/299.61 |
| 4,309,539 | 1/1982 | Boller et al. | 252/299.61 |
| 4,322,354 | 3/1982 | Sorkin | 252/299.61 |
| 4,348,324 | 9/1982 | Demus et al. | 252/299.61 |
| 4,349,452 | 9/1982 | Osman et al. | 252/299.63 |
| 4,398,803 | 8/1983 | Pohl et al. | 252/299.63 |
| 4,400,061 | 8/1983 | Carr et al. | 252/299.63 |
| 4,419,262 | 12/1983 | Petrzilka | 252/299.61 |
| 4,419,263 | 12/1983 | Praefike et al. | 252/299.63 |
| 4,431,853 | 2/1984 | Sato et al. | 252/299.61 |
| 4,432,885 | 2/1984 | Petrzilka et al. | 252/299.61 |
| 4,439,015 | 3/1984 | Rich et al. | 252/299.63 |
| 4,450,094 | 5/1984 | Sato et al. | 252/299.61 |
| 4,460,770 | 7/1984 | Petrzilka et al. | 252/299.63 |
| 4,462,923 | 7/1984 | Boller et al. | 252/299.61 |

FOREIGN PATENT DOCUMENTS

| | | |
|---|---|---|
| 0025119 | 3/1981 | European Pat. Off. ........ 252/299.61 |
| 0031796 | 7/1981 | European Pat. Off. ......... 252/299.6 |
| 56501 | 7/1982 | European Pat. Off. ........ 252/299.61 |
| 58512 | 8/1982 | European Pat. Off. ........ 252/299.62 |
| 0058981 | 9/1982 | European Pat. Off. ........ 252/299.63 |
| 2226376 | 12/1972 | Fed. Rep. of Germany ... 252/299.6 |
| 2257588 | 6/1973 | Fed. Rep. of Germany ........ 252/299.61 |
| 2309501 | 9/1973 | Fed. Rep. of Germany ... 252/299.6 |
| 2334425 | 1/1974 | Fed. Rep. of Germany ........ 252/299.63 |

(List continued on next page.)

OTHER PUBLICATIONS

Libman, N. M. et al., Zh. Org. Khim., vol. 12, (12), pp. 2566-2574, (1976).

Dabrowski, R. et al., Mol. Cryst. Liq. Cryst., vol. 87, pp. 109-135, (1982).

Adomenas, P. et al., Advances in Liq. Cryst. Res. and Appl., Bata, L., Pergamon Press, Oxford, pp. 1029-1038, (1980).

(List continued on next page.)

Primary Examiner—Teddy S. Gron
Attorney, Agent, or Firm—Jon S. Saxe; Bernard S. Leon; George W. Johnston

[57] ABSTRACT

Compounds of the formula

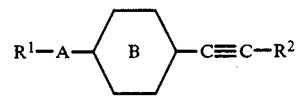

I wherein ring B stands for 1,4-phenylene or a trans-1,4-disubstituted cyclohexane ring and A stands for a group with 1 to 3 six-membered rings, which together with ring B represents a central group of formulae II-XIII; $R^1$ signifies a straight-chain alkyl group containing 1 to 9 carbon atoms or when $R^1$ is attached to a benzene, monofluorinated benzene or pyrimidine, ring $R^1$ also signifies a straight-chain alkoxy group with 1 to 9 carbon atoms; and $R^2$ signifies hydrogen, cyano or a straight-chain alkyl group containing 1 to 7 carbon atoms, their manufacture, liquid crystalline mixtures which contain said compounds and their use for electro-optical purposes are described.

The compounds of formula I are especially valuable as components in liquid crystal mixtures and for the most part themselves have liquid crystalline properties.

70 Claims, No Drawings

FOREIGN PATENT DOCUMENTS

| | | |
|---|---|---|
| 2504641 | 8/1976 | Fed. Rep. of Germany ... 252/299.6 |
| 2626018 | 12/1977 | Fed. Rep. of Germany ........ 252/299.66 |
| 2636684 | 2/1978 | Fed. Rep. of Germany ........ 252/299.63 |
| 3003256 | 8/1980 | Fed. Rep. of Germany ........ 252/299.63 |
| 2944905 | 10/1980 | Fed. Rep. of Germany ........ 252/299.61 |
| 3034222 | 4/1981 | Fed. Rep. of Germany ........ 252/299.63 |
| 2948836 | 6/1981 | Fed. Rep. of Germany ........ 252/299.63 |
| 3006666 | 9/1981 | Fed. Rep. of Germany ........ 252/299.63 |
| 3131593 | 6/1982 | Fed. Rep. of Germany ........ 252/299.62 |
| 3151367 | 7/1983 | Fed. Rep. of Germany ........ 252/299.63 |
| 105701 | 5/1974 | German Democratic Rep. ................ 252/299.63 |
| 52-36642 | 3/1977 | Japan ............ 252/299.66 |
| 585256 | 2/1977 | Switzerland ...... 252/299.6 |
| 614919 | 12/1979 | Switzerland ...... 252/299.5 |
| 2041354A | 9/1980 | United Kingdom ........... 252/299.61 |
| 2044767A | 10/1980 | United Kingdom ........... 252/299.61 |
| 2065104A | 6/1981 | United Kingdom ........... 252/299.62 |
| 2067188 | 7/1981 | United Kingdom ........... 252/299.67 |

OTHER PUBLICATIONS

C.A., vol. 96, 103527p, (1982).
C.A., vol. 96, 95420f, (1982).
Lodewijk, E., C.A., 80, 47707c, (1974).
Lodewijk, E., C.A., 81, 37427t, (1974).
Adomenas et al., Chem. Abstract, 95:219871e, (1981).
Dabrowski et al., Chem. Abstract, 96:95420f, (1982).
Creagh, Linda T., Proceedings of the IEEE, vol. 61, No. 7, Jul. 1973.
Villiger et al., Z. Naturforsch, Synthesis and Mesomorphic Properties of New Liquid Crystalline Cyclohexyl-Phenyl- and Dicyclohexyl-pyrimidines, 34b, 1535-1541, (1979).
Adomenas et al., Advances in Liquid Crystal Research and Applications, 1029, (1980).
Dabrowski et al., Mol. Cryst. Liq. Cryst., 87, 109 (1982).
Dabrowski et al., Chem. Abst., 96:103527p, (1982).

ACETYLENES

BACKGROUND OF THE INVENTION

1. Field of the Invention

This invention relates to liquid crystalline compounds and mixtures.

2. Description of the Art

Liquid crystals have recently gained considerable importance primarily as dielectrics in indicating devices, since the optical properties of such substances can be influenced by an applied voltage. Electro-optical devices based on liquid crystals are well known to the person skilled in the art and can be based on various effects such as, for example, dynamic scattering, deformation of aligned phases (DAP type), the Shadt-Helfrich effect (rotation cell), the guest/host effect or a cholesteric-nematic-type phase transition.

Liquid crystals must satisfy a number of requirements in order to be suitable as dielectrics for electro-optical indicating devices. For example, they must have a good chemical stability towards environmental factors such as, for example, heat, air, moisture and the like, must be colourless, must have short response times and not too high a viscosity, must have a nematic or cholesteric mesophase in all temperature ranges in which the liquid crystal cell is to be operated and must give a good contrast. Other properties such as, for example, the threshold potential, the dielectric anisotropy and the electrical conductivity, must fulfil different conditions depending on the type of cell which is used.

Since, in general, it is not possible to achieve all desired and to some extent contradictory properties with a single compound, attempts have mainly been made to optimize the properties for the particular applications by mixing several compounds or components. In this case it is, however, important that the components undergo no chemical reactions with one another and can be mixed well. Further, the mixtures formed should have no smectic mesophases.

There are already known a series of liquid crystalline compounds which have as wing or terminal groups, for example, alkyl, alkoxy, alkanoyloxy, alkoxycarbonyl and cyano groups. However, a considerable disadvantage of the known liquid crystals is that, in general such compounds with large mesophase ranges are relatively viscous, while other compounds with low viscosity have small mesophase ranges or even only monotropic mesophases.

In the present invention, novel compounds have been found which permit a further improvement of the properties of liquid crystalline dielectrics.

SUMMARY

The present invention concerns phenyl-acetylenes and cyclo-hexylacetylenes of formula I hereinbelow which includes compounds of the formulae:

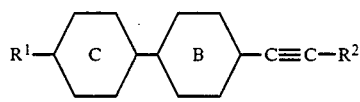
XX

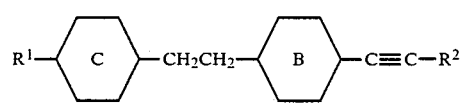
XXI

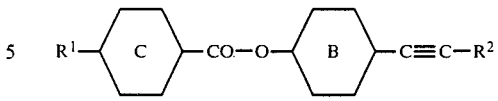
XXII

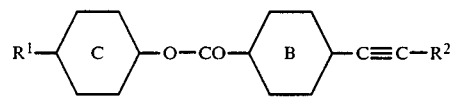
XXIII

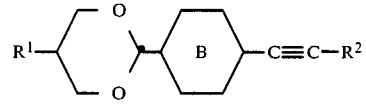
XXIV

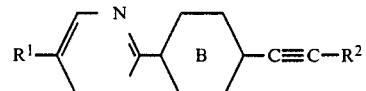
XXV

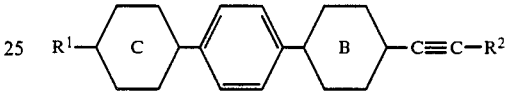
XXVI

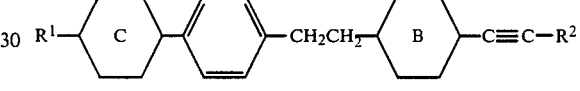
XXVII wherein each of rings B and C signifies, 1,4-phenylene or trans-1,4-substituted cyclohexane; $R^1$ signifies a straight-chain alkyl group containing 1 to 9 carbon atoms or when $R^1$ is attached to a benzene or pyrimidine ring $R^1$ also signifies a straight-chain alkoxy group containing 1 to 9 carbon atoms; $R^2$ signifies hydrogen, cyano or a straight-chain alkyl group containing 1 to 7 carbon atoms; with the proviso that rings B and C in formula XX do not simultaneously signify 1,4-phenylene and with the further proviso that ring B in formula XXV does not signify 1,4-phenylene when $R^2$ represents hydrogen or cyano.

DETAILED DESCRIPTION OF THE PRESENT INVENTION

The present invention is concerned with novel phenyl-acetylenes and cyclohexylacetylenes of the formula

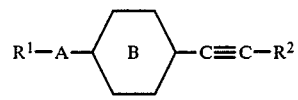
I wherein ring B is 1,4-phenylene or a trans-1,4-disubstituted cyclohexane ring and A is a group with 1 to 3 six-membered rings, which together with ring B comprises a central group within formula I of the formula;

(a)

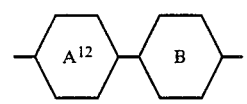
II wherein ring $A^{12}$ signifies trans-1,4-di-substituted cyclohexane, 1,4-di-substituted bicyclo[2.2.2]octane, trans-2,5-disubstituted 1,3-dioxane linked in the 2-position with ring B or, when ring B represents trans-1,4-disubstituted cyclohexane or $R^2$ represents alkyl, ring $A^{12}$ also signifies 1,4-phenylene, fluoro-1,4-phenylene, 3,6-disubstituted pyridazine or 2,5-disubstituted pyrimidine linked in the 2-position with ring B;

(b)

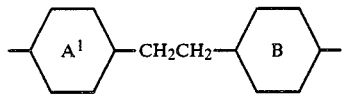  III wherein ring $A^1$ signifies 1,4-phenylene, fluoro-1,4-phenylene, trans-1,4-disubstituted cyclohexane, 1,4-disubstituted bicyclo[2.2.2]octane, 3,6-disubstituted pyridazine, trans-2,5-disubstituted 1,3-dioxan or 2,5-disubstituted pyrimidine linked in the 2-position with the ethylene group in formula III;

(c)

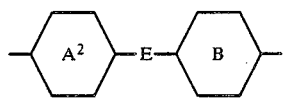  IV wherein ring $A^2$ signifies 1,4-phenylene, fluoro-1,4-phenylene, trans-1,4-disubstituted cyclohexane or 1,4-disubstituted bicyclo[2.2.2]octane and E signifies an ester group;

(d)

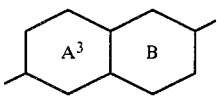  V wherein ring $A^3$ together with ring B is 2,6-disubstituted tetralin or 2,6-di(equatorially substituted) trans-decalin;

(e)

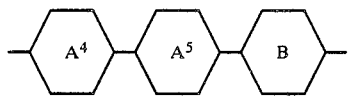  VI wherein (i) one of rings $A^4$, $A_5$ and B signifies 1,4-phenylene and each of the other rings signifies 1,4-phenylene or trans-1,4-disubstituted cyclohexane; or (ii) ring $A^5$ signifies pyridazine or pyrimidine linked in the 2-position with ring B and rings $A^4$ and B each signify 1,4-phenylene or trans-1,4-disubstituted cyclohexane; or (iii) $A^4$ signfies 1,4-phenylene, ring A signifies 1,3-dioxane trans-linked in the 2-position with ring B and ring B signifies 1,4-phenylene or trans-1,4-disubstituted cyclohexane;

(f)

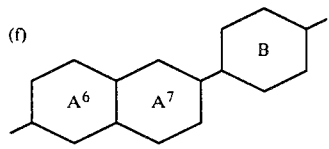  VII wherein ring $A^6$ and $A^7$ together signify 2,6-disubstituted naphthalene, 2,6-disubstituted tetralin or 2,6-di(equatorially substituted) trans-decalin;

(g)

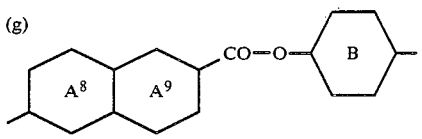  VIII wherein rings $A^8$ and $A^9$ together signify 2,6-disubstituted naphthalene, 2,6-disubstituted tetralin or 2,6-di(equatorially substituted) trans-decalin;

(h) 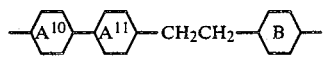  IX (i) 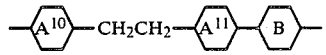  X (j) 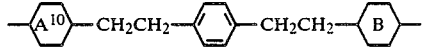  XI (k) 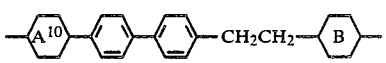  XII or (l) 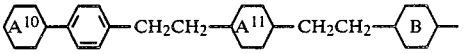  XIII wherein rings
$A^{10}$, $A^{11}$ and B each signify 1,4-phenylene or trans-1,4-disubstituted cyclohexane;
$R^1$ signifies a straight-chain alkyl group containing 1 to 9 carbon atoms or when the central group is such that $R^1$ is attached to a benzene, monofluorinated benzene or pyrimidine ring, $R^1$ also signifies a straight-chain alkoxy group containing 1 to 9 carbon atoms; and
$R^2$ signifies hydrogen, cyano or a straight-chain alkyl group containing 1 to 7 carbon atoms.

The invention is also concerned with a process for the manufacture of the compounds of formula I above, liquid crystalline mixtures which contain compounds of formula I as well as their use for electro-optical purposes.

Unless otherwise stated, "alkyl" denotes a straight-chain alkyl group of 1 to 12 carbon atoms or a branched-chain alkyl group of 1 to 12 carbon atoms. Exemplary straight-chain alkyl groups are methyl, ethyl, propyl, butyl, pentyl, hexyl, heptyl, octyl, nonyl, decyl, undecyl and dodecyl. Exemplary branched-chain alkyl groups are isopropyl, isobutyl, sec-butyl, 1-methylbutyl, 2-methylbutyl 3-methylpentyl, 4-methylhexyl and isopentyl. Lower alkyl denotes straight-chain and branched-chain alkyl groups of 1 to 5 carbon atoms.

The term "alkoxy" as well as any other groups in the specification containing "alkyl" denote moieties in which their "alkyl" portions are as defined previously. In particular, straight-chain alkoxy groups denote moieties having a straight-chain alkyl portion as previously defined. Exemplary straight-chained alkoxy groups are methoxy, ethoxy, propyloxy, butyloxy, pentyloxy, hexyloxy, heptyloxy, octyloxy or nonyloxy.

The term "halogen" denotes fluorine, chlorine, bromine or iodine. The term "alkali metal" denotes sodium, potassium or lithium. The term "benzene ring" denotes 1,4-phenylene or, in connection with fused rings (formulae V, VII and VIII), also denotes a benzene moiety in 2,6-disubstituted naphthalene or 2,6-disubstituted tetralin.

The groups of formulae II-XIII (i.e. the ring systems consisting of A and ring B) are referred to herein as central groups and the groups R¹ and —C≡C—R² are referred to herein as wing groups. In accordance with the foregoing definition the central group of formula I has at least two and at most four six-membered rings, whereby in the case of the central groups of formulae V, VII and VIII two rings can also be fused (condensed ring system) and can together form naphthalene, tetralin (1,2,3,4-tetrahydronaphthalene) or trans-decalin (trans-decahydronaphthalene) with an equatorial arrangement of the substituents.

The expression "ester group E" signifies the groups —CO—O— and —O—CO—.

It has now surprisingly been found that the compounds provided by the invention for the most part are themselves liquid crystalline and predominantly have a nematic mesophase. Especially surprising is, moreover, the fact that the introduction of the acetylene group into the wing group of the compounds provided by the invention leads in general to a distinct extension of the mesophase range or to an increase of the clearing point. In addition, in certain cases an intensification of the nematic tendencies has been observed. Further, it is remarkable that the remaining characteristic properties of the individual classes of compound such as, for example, the low viscosity of the phenylcyclohexanes, the low threshold potential of the phenyldioxanes or the dielectric anisotropy of the phenylpyrimidines largely remains. In addition, the compounds provided by the invention have a satisfactory to good UV stability.

This influence of the acetylene group on the properties of the compounds provided by the invention results in liquid crystals with large mesophase ranges which (in comparison to known liquid crystals with similar high mesophase ranges) have improved properties, especially improved viscosities and response times. On the other hand, compounds which have only a small or monotropic mesophase range such as the phenyldioxanes, the phenylpyrimidines, the cyclohexanecarboxylic acid phenyl esters and the like (which, however, because of other favourable properties have often been used in mixtures) can now be replaced by corresponding compounds provided by the invention which have similar favourable properties and at the same time an extended mesophase range. Furthermore, a series of compounds which come into consideration as doping agents for liquid crystal mixtures, but which themselves have no liquid crystalline properties (e.g. 2,6-disubstituted tetralins and trans-decalins and many phenylcyclohexanes), can be replaced by corresponding compounds provided by the invention which themselves have liquid crystalline properties or at least give a lower clearing point depression in mixtures.

Moreover, the present invention greatly increases the choice of suitable liquid crystalline compounds with the widest variety of properties and this substantially facilitates the optimization of properties of mixtures.

The following formulae are examples of groups of compounds provided by the invention falling under formula I above:

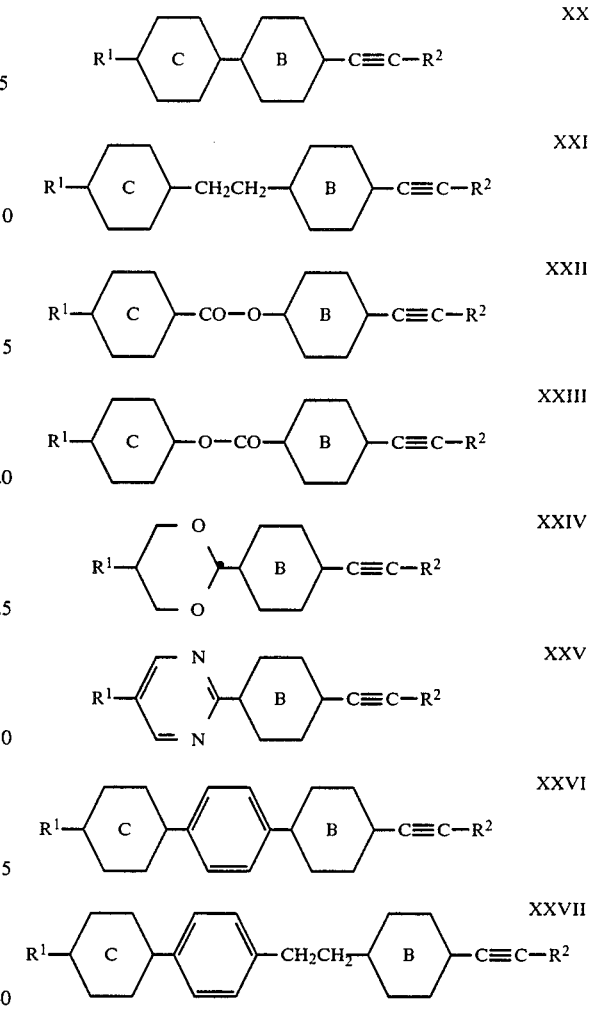

wherein rings B and C signify 1,4-phenylene or trans-1,4-disubstituted cyclohexane and R¹ and R² have the significances given above, with the provisos that rings B and C in formula XX do not simultaneously signify 1,4-phenylene and that ring B in formula XXV does not signify 1,4-phenylene when R² represents hydrogen or cyano.

Table I illustrates the change of the mesophase range or of the mesophase type of some representative compounds provided by the invention. The data for the structure of the compounds relates to formulae XX-XXVII above, whereby "a" (aromatic) signifies 1,4-phenylene and "s" (saturated) signifies a trans-1,4-disubstituted cyclohexane ring. Comparative compounds (insofar as R² signifies the cyano group) differ from the compound provided by the invention only by the absence of the acetylene group. In order to compensate for the influence of the chain length, the remaining compounds were compared with those compounds which have the group —CH₂CH₂— in place of the group —C≡C—. N denotes a nematic mesophase type and S denotes a smectic mesophase type. Monotropic clearing points have been placed in parentheses and extrapolated virtual clearing points have been denoted with an asterisk (*). The extent of the mesophase ranges (ΔT) as well as the melting points and clearing points are given in °C.

TABLE 1

| Formula | Ring B | Ring C | $R^1$ | $R^2$ | Compound of formula I | | | | Comparative compound | | | |
|---|---|---|---|---|---|---|---|---|---|---|---|---|
| | | | | | M.p. | cl.p. | Δ T | Mesophase | M.p. | cl.p. | Δ T | Mesophase |
| XX | a | a | $C_5H_{11}$ | $CH_3$ | 60.5 | 83.4 | 22.9 | S | 47.6 | | | None |
| XX | a | s | $C_5H_{11}$ | H | 39.4 | 42.1 | 2.7 | N | −1.5 | (−75)* | −73.5 | None |
| XX | a | s | $C_5H_{11}$ | CN | 49.7 | 128.9 | 79.2 | N | 32 | 55 | 23 | N |
| XX | a | s | $C_5H_{11}$ | $CH_3$ | 41.6 | 64.9 | 23.3 | N | −9.3 | (−11.9) | −2.6 | N |
| XX | a | s | $C_5H_{11}$ | $C_2H_5$ | 29.5 | 31.4 | 1.9 | N | | | | |
| XX | a | s | $C_5H_{11}$ | $C_3H_7$ | 20.0 | 31.3 | 11.3 | N | | | | |
| XX | s | a | $C_5H_{11}$ | CN | 46.9 | (45.4) | −1.5 | N | 16.3 | | | None |
| XXI | a | s | $C_5H_{11}$ | H | 25.5 | 42.5 | 17.0 | N | | | | |
| XXI | a | s | $C_5H_{11}$ | CN | 36.7 | 105.5 | 68.8 | N | 30.9 | 52.5 | 21.6 | N |
| XXI | a | s | $C_5H_{11}$ | $CH_3$ | 46.8 | 55.3 | 8.5 | N | 4.5 | 18 | 13.5 | S |
| XXI | a | s | $C_4H_9$ | $C_2H_5$ | 6.1 | 9.5 | 3.4 | N | | | | |
| XXI | a | s | $C_4H_9$ | $C_3H_7$ | 14.3 | 22.6 | 8.3 | | | | | |
| XXI | s | a | $C_5H_{11}$ | CN | 36.5 | 43.0 | 6.5 | N | 22.4 | (−14.1) | −36.5 | N |
| XXI | s | a | $C_4H_9O$ | CN | 66.6 | 76.7 | 10.1 | N | 35.6 | (19.0) | −16.6 | N |
| XXI | s | a | $C_4H_9O$ | $C_3H_7$ | 21.6 | 25.3 | 3.7 | S | 25.5 | 45.0 | 19.5 | S |
| XXI | s | s | $C_5H_{11}$ | H | 51.3 | 68.0 | 16.7 | N | | | | |
| XXI | s | s | $C_5H_{11}$ | CN | 51.4 | 112.7 | 61.3 | N | 56.2 | 72.3 | 16.1 | N |
| XXII | a | s | $C_5H_{11}$ | H | 50.6 | 78.5 | 27.9 | N | 42.0 | (29.0) | −13.0 | N |
| XXII | a | s | $C_5H_{11}$ | CN | 76.8 | 153.2 | 76.4 | N | 47 | 79 | 32 | N |
| XXIII | s | a | $C_6H_{13}O$ | H | 49.8 | (34.5) | −15.3 | N | 32 | 45 | 13 | N |
| XXIII | s | s | $C_5H_{11}$ | H | 54.2 | (40.5) | −13.7 | N | 20.5 | 35.0 | 14.5 | S |
| XXIV | a | | $C_5H_{11}$ | CN | 60.3 | 111.0 | 50.7 | N | 56.4 | (47.9) | −8.5 | N |
| XXVII | s | a | $C_5H_{11}$ | H | 66.0 | 126.4 | 60.4 | S/N | 43.5 | 141.1 | 97.6 | S/N |

Preferred central groups in the compounds of formula I are the groups of formulae II, III, IV, VI, IX and X above, especially those of formulae II, III and IV. The compounds of formulae XX-XXV above are especially preferred. In formula XX one of rings B and C preferably signifies trans-1,4-disubstituted cyclohexane and the other signifies 1,4-phenylene and in formula XXI at least one of rings B and C preferably signifies trans-1,4-disubstituted cyclohexane.

Further, there are preferred, those compounds of formula I in which ring B is saturated, i.e. ring B represents trans-1,4-disubstituted cyclohexane or in the central group of formula V ring B together with ring $A^3$ represents tetralin or trans-decalin. However, in formulae XXII and XXIII ring B can preferably also signify 1,4-phenylene. Further, those compounds of formula I in which ring B is aromatic $R^2$ signifies alkyl are preferred.

$R^2$ preferably signifies hydrogen, cyano, methyl, ethyl or propyl, especially hydrogen, cyano or methyl. $R^1$ preferably signifies a straight-chain alkyl group containing 3 to 7 carbon atoms or a straight-chain alkoxy group containing 2 to 6 carbon atoms.

Also preferred are compounds of formula I wherein A together with ring B represents:

(a) a central group of formula II in which ring $A^{12}$ signifies trans-1,4-disubstituted cyclohexane, trans-2,5-disubstituted 1,3-dioxane linked in the 2-position with ring B or, when ring B represents trans-1,4-disubstituted cyclohexane or $R^2$ represents alkyl, ring $A^{12}$ also signifies 1,4-phenylene or 2,5-disubstituted pyrimidine linked in the 2-position with ring B, or (b) a central group of formula III in which ring $A^1$ signifies 1,4-phenylene or trans-1,4-disubstituted cyclohexane, or (c) a central group of formula IV in which ring $A^2$ signifies 1,4-phenylene or trans-1,4-disubstituted cyclohexane and E signifies an ester group.

The compounds of formula I named in the Examples of this case illustrate preferred compounds.

The compounds of formula I can be manufactured in accordance with the following process:

(a) for the manufacture of compounds of formula I in which $R^2$ signifies hydrogen, reacting a compound of the formula

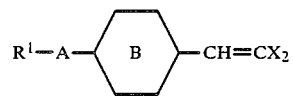

XIV wherein X denotes chlorine or bromine and A, B and $R^1$ have the above significances, with base or lithium amalgam and subsequently hydrolyzing the reaction product, or (b) for the manufacture of compounds of formula I in which $R^2$ signifies cyano, reacting a compound of formula I in which $R^2$ signifies hydrogen with base and subsequently with phenyl cyanate, or (c) for the manufacture of compounds of formula I in which $R^2$ signifies a straight-chain alkyl group, reacting a compound of formula I in which $R^2$ signifies hydrogen with base and subsequently with an alkyl bromide or alkyl iodide, or (d) for the manufacture of compounds of formula I in which A together with ring B signifies a central group of formula IV and E signifies the ester group —CO—O—, esterifying a compound of the formula

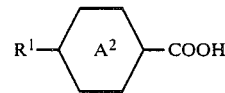

XV wherein $A^2$ and $R^1$ have the above significances, or a reactive derivative thereof with a compound of the formula

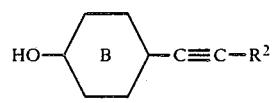

XVI wherein B and $R^2$ have the above significances, or a suitable salt thereof, or (e) for the manufacture of compounds of formula I in which A together with ring B signifies a central group of formula IV and E signifies the ester group —O—CO—, esterifying a compound of the formula

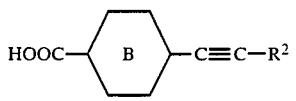

XVII wherein B and $R^2$ have the above significances, or a reactive derivative thereof with a compound of the formula

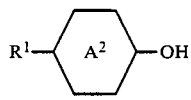

XVIII wherein $A^2$ and $R^1$ have the above significances, or a suitable salt thereof, or (f) for the manufacture of compounds of formula I in which A together with ring B signifies a central group of formula VIII, esterifying a compound of the formula

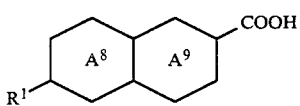

XIX wherein $A^8$, $A^9$ and $R^1$ have the above significances, or a reactive derivative thereof with a compound of formula XVI above or a suitable salt thereof.

The reaction of a compound of formula XIV in accordance with process variant (a) can be carried out in a manner known per se. Butyl lithium, lithium amide, sodium amide and the like are preferred bases. Liquid ammonia is conveniently used as the solvent when the base is lithium amide or sodium amide and an inert organic solvent, preferably an ether such as diethyl ether or tetrahydrofuran, is conveniently used as the solvent in the remaining cases. However, the reaction can also be carried out reductively using lithium amalgam instead of base. Lithium amide or sodium amide is conveniently used for the reaction of compounds of formula XIV which contain a pyrimidine or pyridazine ring and lithium amide, sodium amide or lithium amalgam is conveniently used for the reaction of compounds of formula XIV which contain an ester group. Pressure and temperature are not critical aspects in this reaction. In general, atmospheric pressure and a temperature between about −80° C. and about 0° C. are used. The subsequent hydrolysis is preferably carried out with water, aqueous ammonium chloride solution and the like.

The reaction of a compound of formula I in which $R^2$ signifies hydrogen with base and phenyl cyanate in accordance with process variant (b) can be carried out in a manner known per se. Butyl lithium, lithium diisopropylamide, lithium amide, sodium amide and the like are preferred bases. Liquid ammonia is conveniently used as the solvent when the base is lithium amide or sodium amide and an inert organic solvent, preferably an ether such as diethyl ether or tetrahydrofurn, is conveniently used as the solvent in the remaining cases. Lithium diisopropylamide is the preferred base for the reaction of compounds which contain a pyrimidine or pyridazine ring and lithium amide or sodium amide is the preferred base for the reaction of compounds which contain an ester group. Temperature and pressure are not critical; in general, however, a temperature between about −80° C. and about −40° C. and atmospheric pressure are preferred.

The reaction of a compound of formula I in which $R^2$ signifies hydrogen with base and an alkyl bromide or alkyl iodide in accordance with process variant (c) can also be carried out according to methods known per se, whereby the bases and solvents referred to in connection with process variant (b) can be used. Hexamethylphosphoric acid triamide is preferably added to the reaction mixture prior to the alkylation with the alkyl bromide or alkyl iodide. Atmospheric pressure and a temperature between about −45° C. and the reflux temperature of the reaction mixture are conveniently used.

The esterifications in accordance with process variants (d), (e) and (f) can be carried out in a manner known per se. Reactive derivatives of the acids of formulae XV, XVII and XIX are the acid chlorides, bromides and anhydrides. Suitable salts of the alcohols of formulae XVI and XVIII are, for example, the alkali metal salts, especially the sodium salt. The reaction of an alcohol and a carboxylic acid can be carried out, for example, in the presence of a catalytic amount of a strong acid (e.g. sulphuric acid or hydrohalic acid) in the presence or absence of an inert organic solvent. A further method is, for example, the reaction of an acid chloride with an alcohol in the presence of an inert organic solvent such as, for example, diethyl ether, tetrahydrofuran, dimethylformamide, benzene, cyclohexane or carbon tetrachloride and/or an acid-binding agent (e.g. a pyridine). However, the esterification of a carboxylic acid with an alcohol in the presence of N,N'-dicyclohexylcarbodiimide and 4-(dimethylamino)pyridine is preferred. Temperature and pressure are not critical; in general, these esterifications are carried out at atmospheric pressure and a temperature between froom temperature (23° C.) and the boiling point of the esterification mixture. The acid halides and anhydrides can be prepared in a manner known per se; for example, acid chlorides are obtained by reacting the corresponding acid with phosphorus trichloride, phosphorus pentachloride, thionyl chloride and the like and anhydrides are obtained by reacting the corresponding acid with acetic anhydride, acetyl chloride, ethyl chloroformate and the like.

The preparation of the compounds of formula XIV and their further reaction in accordance with process variants (a)–(c) is illustrated in Scheme 1 hereinafter in which A, B, $R^1$ and X have the above significances, Y stands for bromine or iodine and R signifies a straight-chain alkyl group containing 1 to 7 carbon atoms.

Scheme 1

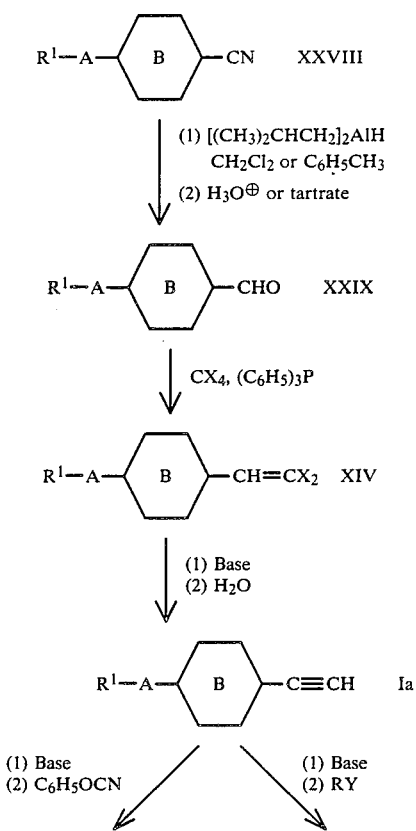

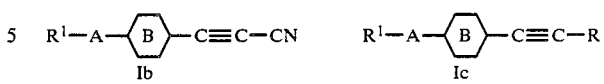

If the compound of formula XXVIII contains an ester group, then this is reductively cleaved during the reaction with diisobutylaluminium hydride. Accordingly, in this case the reaction is carried out using a corresponding cyano-alcohol or a corresponding cyano-carboxylic acid as the starting material and then the aldehyde obtained is esterified in a manner known per se to give the compound of formula XXIX.

The compounds of formula XIV which have no ester group and no pyrimidine or pyridazine ring can, for example, also be converted directly into compounds of formula Ib using butyl lithium and subsequently phenyl cyanate. Further, the compounds of formula XIV can, for example, also be converted directly into compounds of formula Ic using sodium amide in ammonia and an alkyl bromide or alkyl iodide.

The compounds of formula I which contain a pyrimidine or dioxane ring can also be manufactured by firstly introducing the acetylene group and subsequently forming the heterocyclic ring. Examples of such reactions as well as the preparation of the compounds of formulae XXXIV and XXXV (i.e. the compounds of formulae XVI and XVII in which $R^2$ signifies hydrogen) are outlined in Scheme 2 hereinafter in which B and $R^1$ have the above significances and Ts denotes the p-tosyl group.

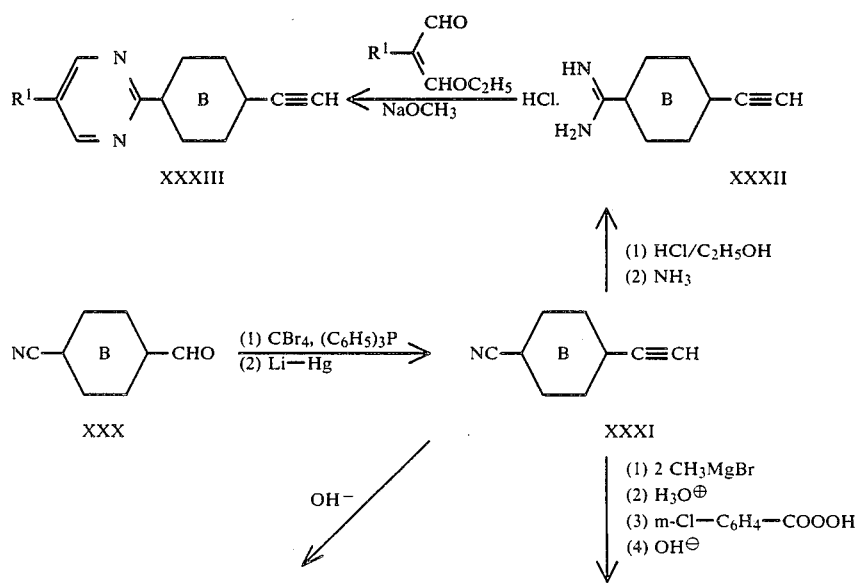

Scheme 2

-continued

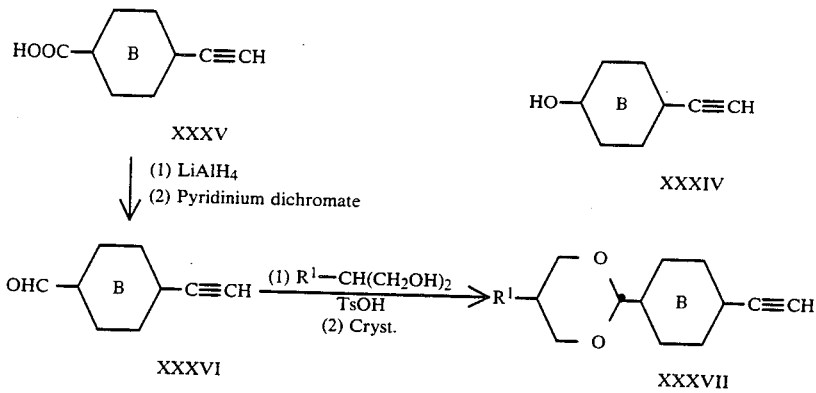

The compound of formula XXXV can be prepared starting not only from the compound of formula XXX, but also from the corresponding compound which contains the methoxycarbonyl group in place of the cyano group.

In order to proceed to the compounds of formulae XVI and XVII in which $R^2$ signifies cyano or alkyl, the compounds of formulae XXXIV and XXXV are reacted with base and phenyl cyanate or an alkyl bromide or alkyl iodide in analogy to process variants (b) and (c) described above. It is, however, also possible firstly to esterify the compounds of formulae XXXIV and XXXV in analogy to process variants (d)–(f) above and subsequently to introduce the cyano or alkyl group.

Further, the compounds of formula XVI in which $R^2$ signifies hydrogen or alkyl can be prepared by converting the hydroxy group of p-hydroxybenzaldehyde or trans-4-hydroxycyclohexanecarboxaldehyde into the tetrahydropyranyloxy group in a manner known per se (e.g. with dihydropyran in methylene chloride in the presence of p-toluenesulphonic acid), then converting the formyl group into an alkynyl group in an analogous manner to Scheme 1 and finally hydrolyzing the resulting compound with acid (e.g. aqueous sulphuric acid) in order to cleave off the tetrahydropyranyl group.

p-(1-Alkynyl)benzaldehydes and trans-4-(1-alkynyl)-cyclohexanecarboxaldehydes can also be prepared, for example, by converting the formyl group in p-(diethoxymethyl)benzaldehyde or trans-(diethoxymethyl)cyclohexanecarboxaldehyde into an alkynyl group in an analogous manner to Scheme 1 and then hydrolyzing the acetyl group (e.g. with aqueous sulphuric acid). The resulting aldehydes can then be converted into the corresponding 1,3-dioxanes in an analogous manner to Scheme 2 or can be oxidized by Jones' oxidation to give compounds of formula XVII in which $R^2$ signifies hydrogen or alkyl.

Further, 4-iodophenol can be converted with ethynyl-trimethylsilane in the presence of bis-(triphenylphosphine)-palladium (II) dichloride, copper (I) iodide and triethylamine into p-[(trimethylsilyl)ethynyl]-phenol. This compound can then be reacted further; for example with potassium hydroxide in methanol/water to give p-ethynylphenol (the compound of formula XXXIV in which ring B is aromatic) or with methyl lithium in tetrahydrofuran/hexamethylphosphoric acid triamide and phenyl cyanate to give (p-hydroxyphenyl)propiolonitrile (a compound of formula XVI in which ring B is aromatic and $R^2$ signifies cyano).

The nitriles of formula XXVIII are for the most part known or can be prepared in analogy to known compounds. The preparation of the remaining compounds of formula XXVIII is illustrated by Schemes 3–12 hereinafter in which B and $R^1$ have the above significances, ring C stands for 1,4-phenylene or trans-1,4-disubstituted cyclohexane, R signifies a straight-chain alkyl group containing 1 to 8 carbon atoms, Ts signifies the p-tosyl group and the broken line (———) indicates that one of the bonds denoted thereby is a double bond.

Scheme 3

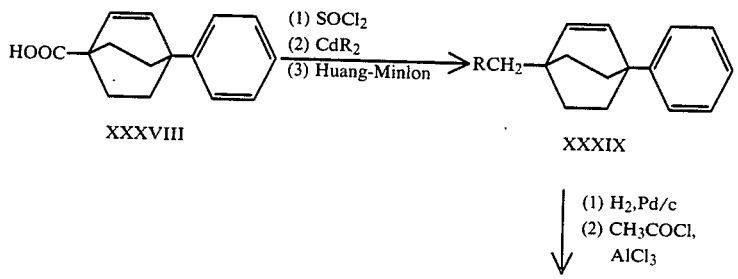

4,528,114
Scheme 3
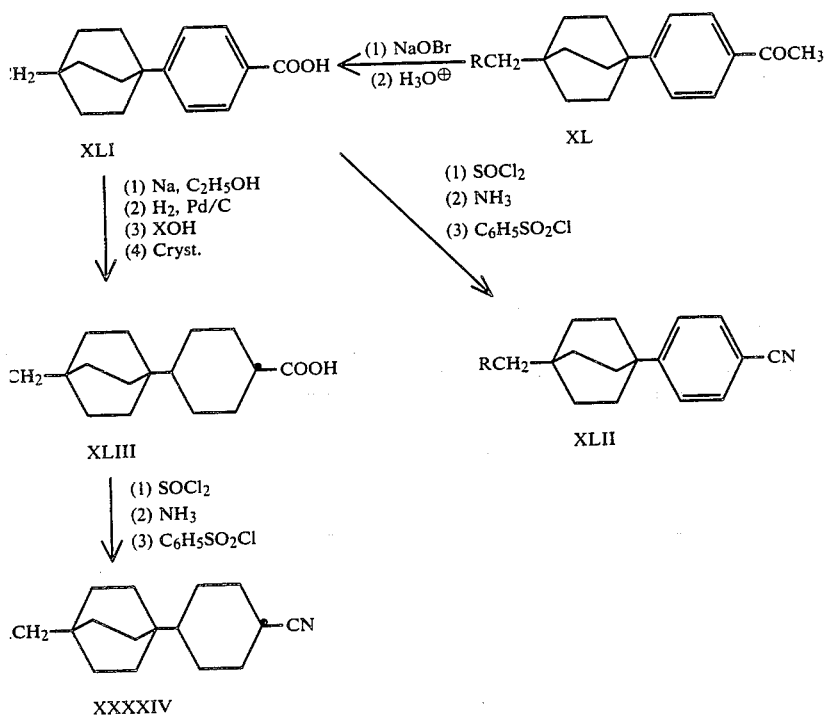
Scheme 4
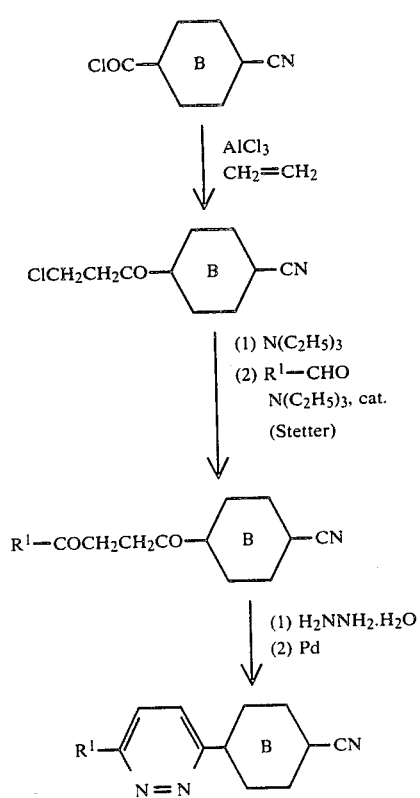
Scheme 5
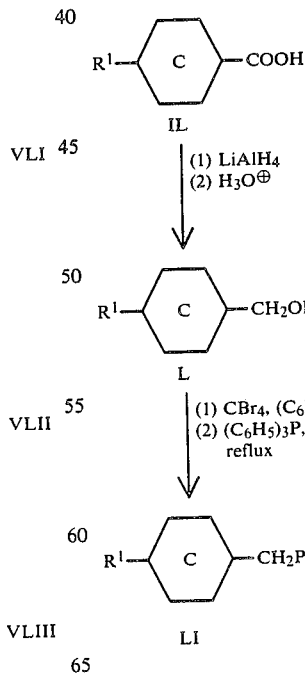
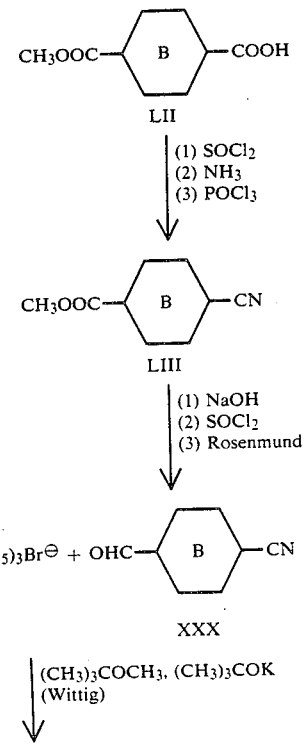

4,528,114
Scheme 6
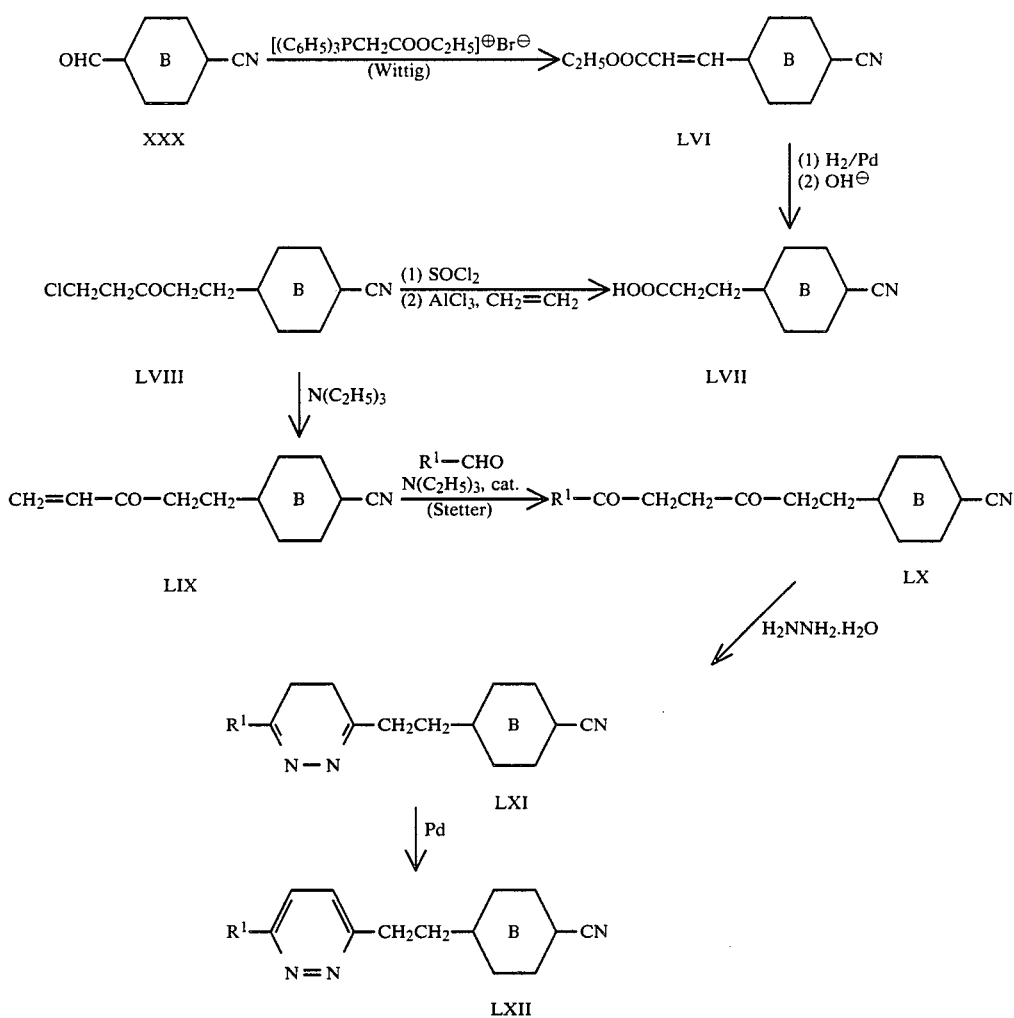
-continued
Scheme 5
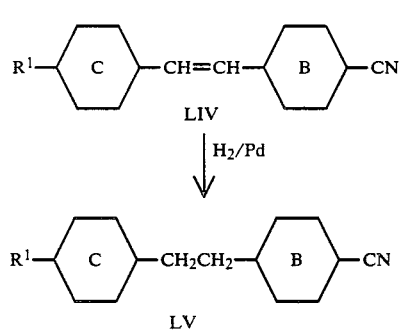
Scheme 7
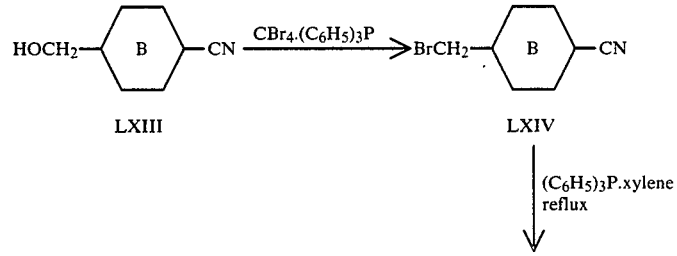

Scheme 7
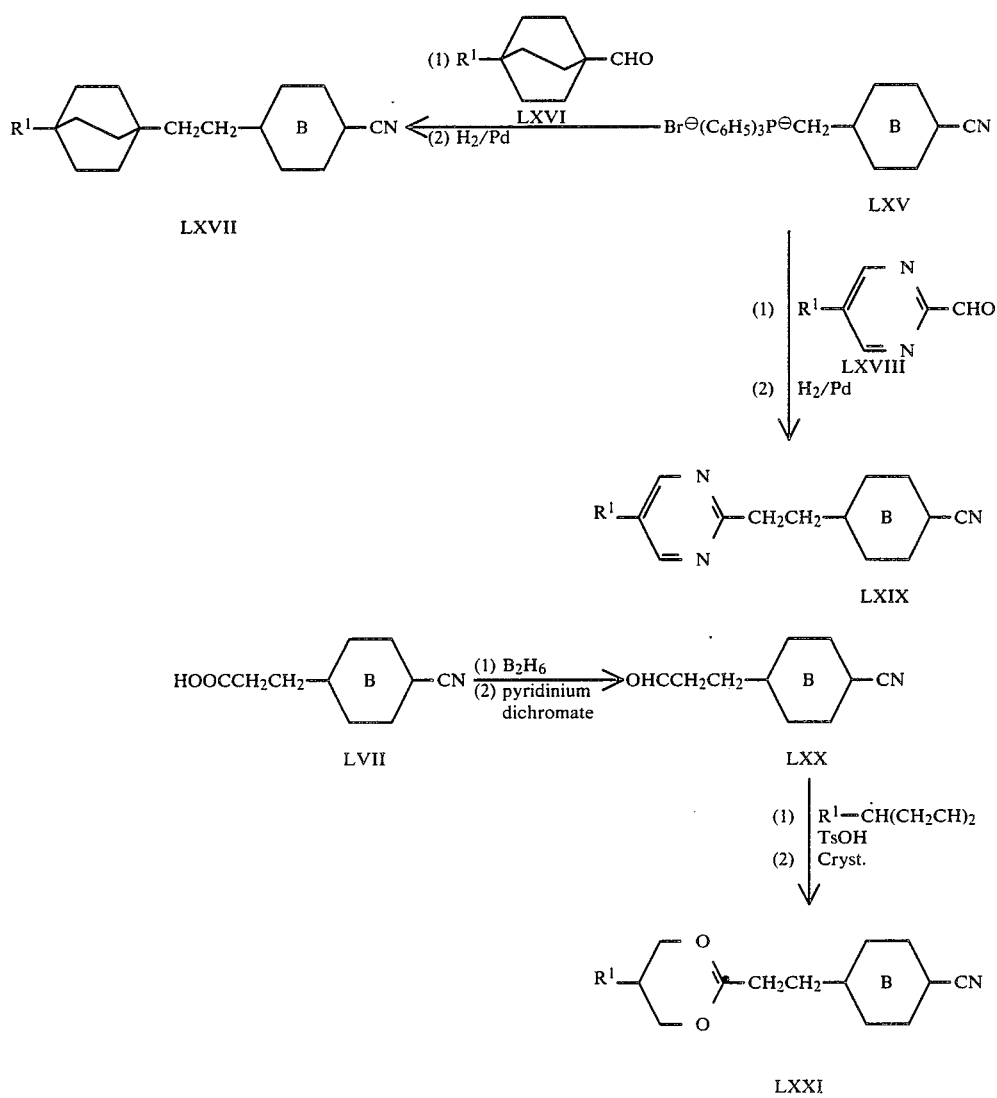
Scheme 8
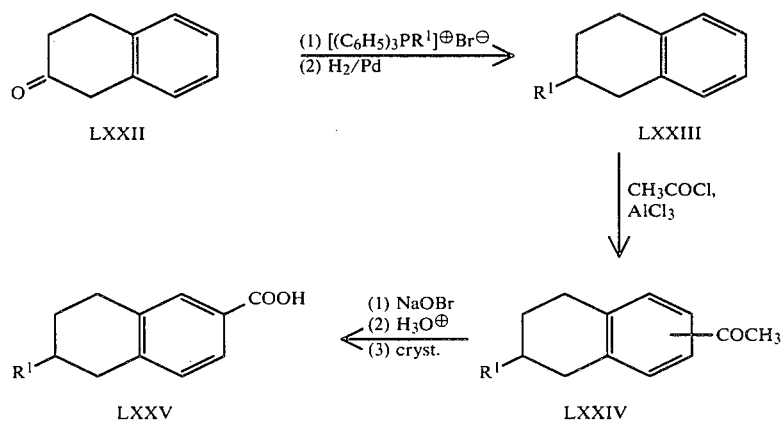

Scheme 8
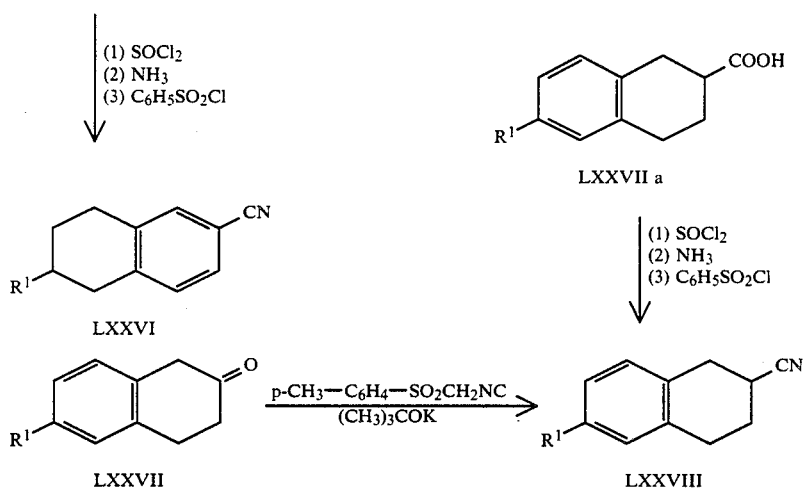
Scheme 9
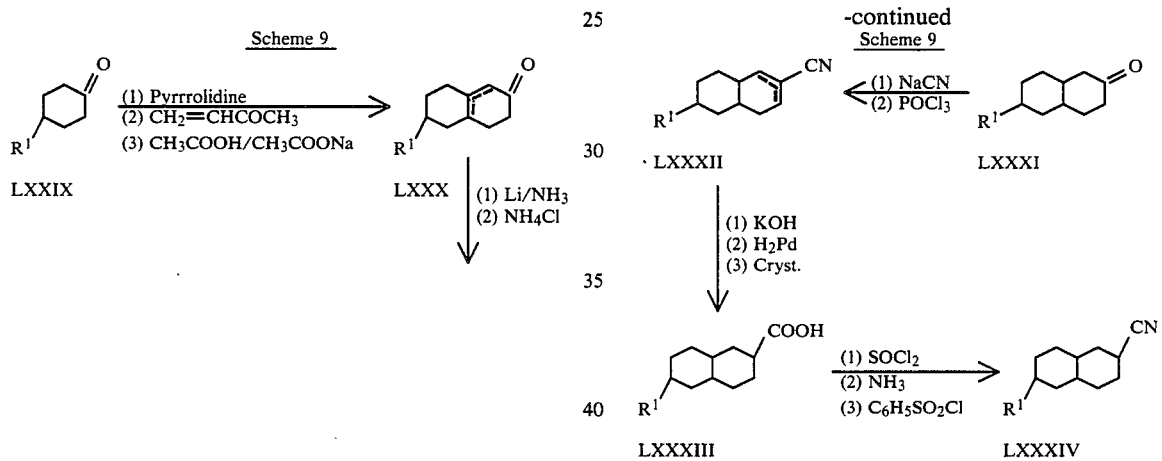
Scheme 10
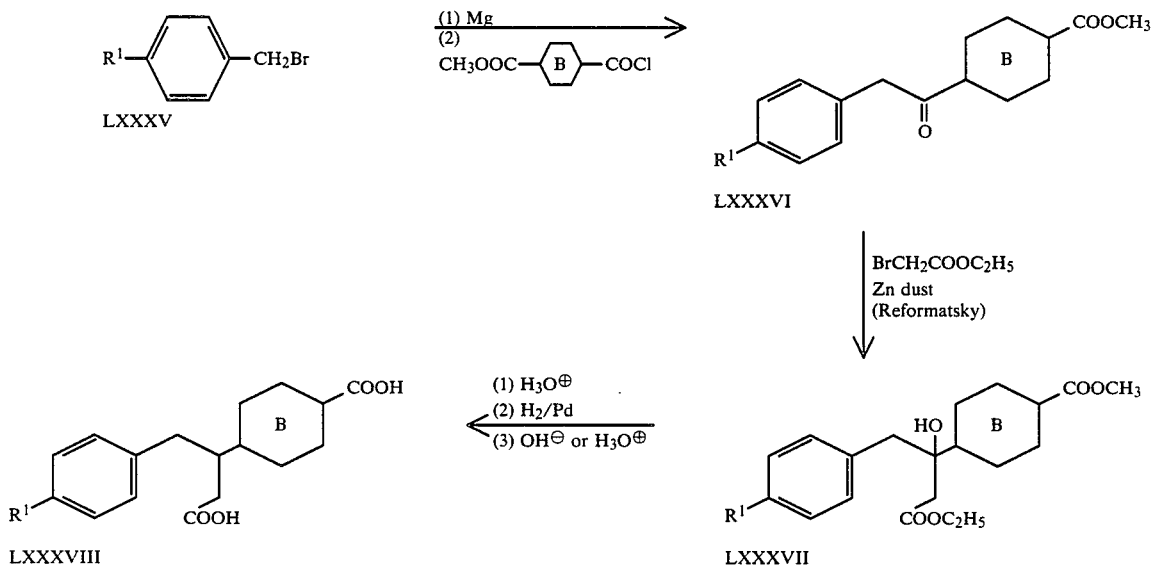

4,528,114
-continued
Scheme 10
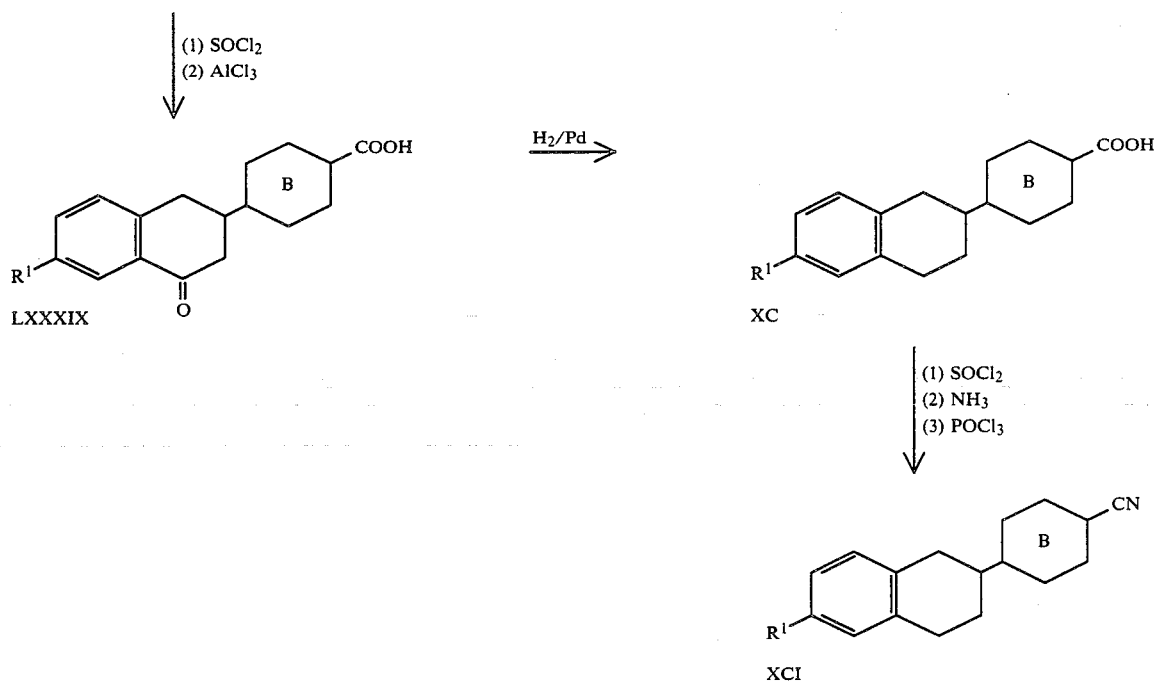
Scheme 11
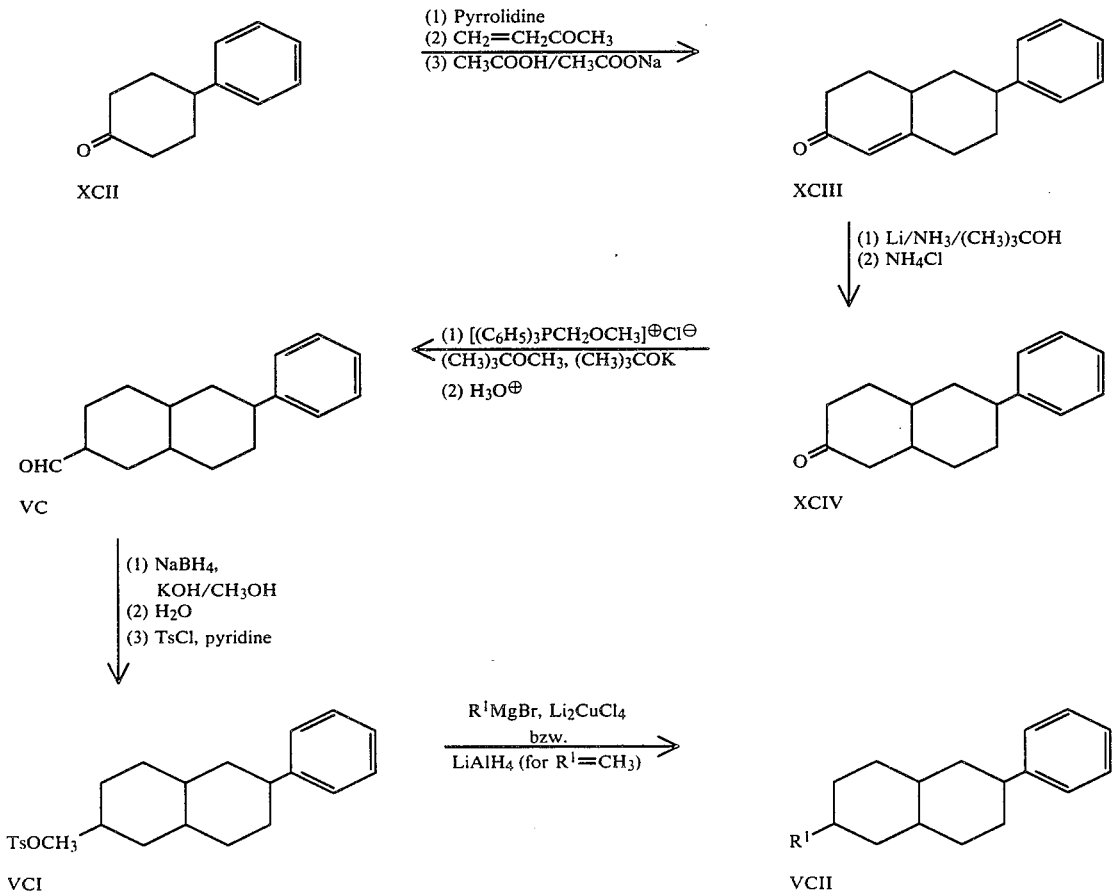

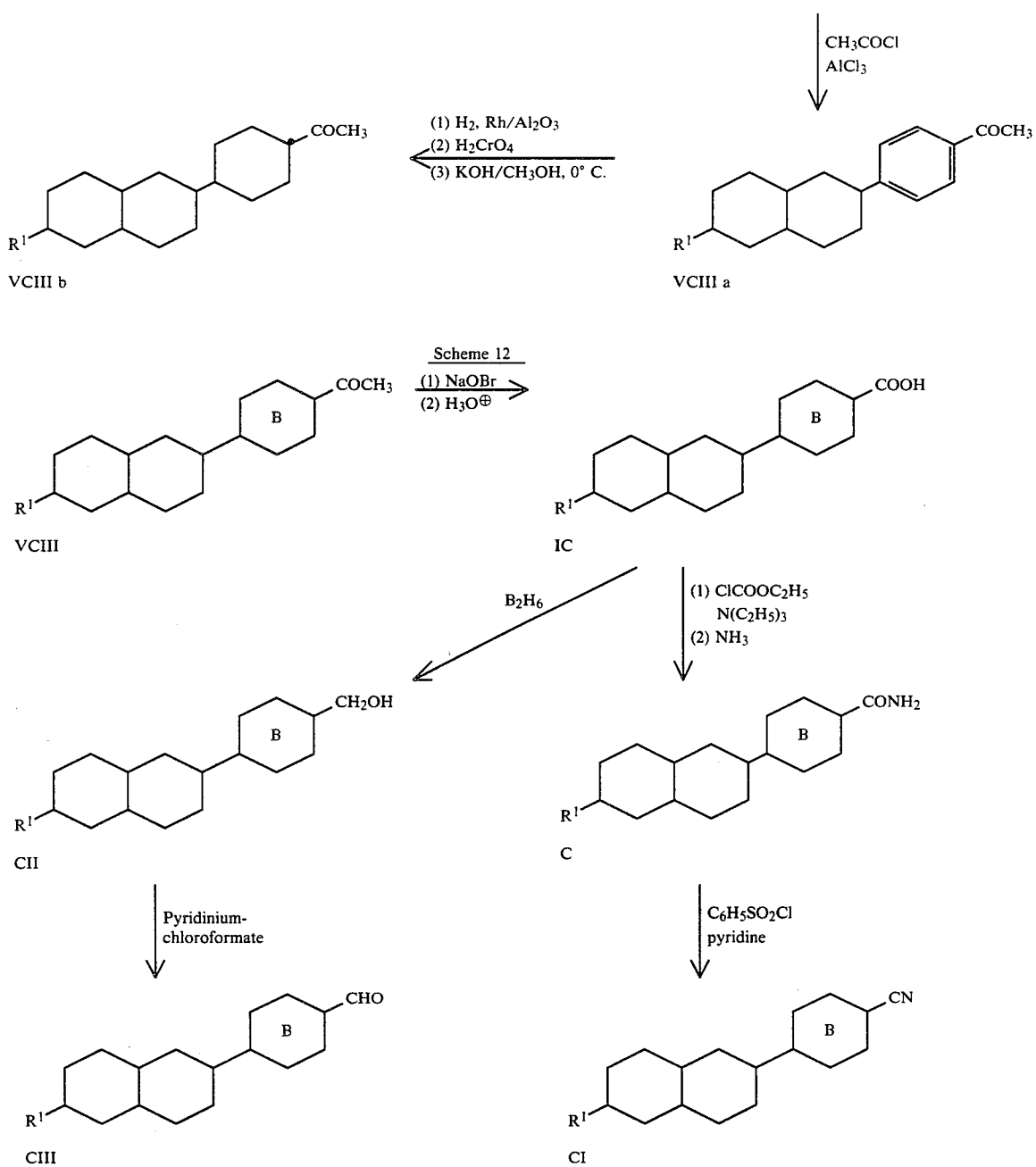

3-Benzyl-5-(2-hydroxyethyl)-4-methyl-1,3-thiazolium chloride is the preferred catalyst in the reaction of the compounds of formulae VLI and LIX according to Stetter. (Chem. Ber. 114 (1981) 581).

In the Wittig reaction for the preparation of the compounds of formula LIV it is possible to start either from the compounds of formulae XXX and LI (as described in Scheme 5) or from the corresponding compounds in which the reactive groups are interchanged, i.e. the formyl group is situated on ring C and the group —CH$_2$P$^+$(C$_6$H$_5$)$_3$Br$^-$ is situated on ring B. If one of rings B and C is aromatic and the other is saturated, the Wittig reaction is preferably carried out using compounds which have the formyl group on the saturated ring and the group —CH$_2$P$^+$(C$_6$H$_5$)$_3$Br$^-$ on the aromatic ring. Those compounds of formula XXVIII in which A and ring B together represent a central group of formulae IX-XIII can also be prepared in an analogous manner. The starting materials for the Wittig reaction are conveniently prepared in this case from the corresponding nitriles, for example by reducing the cyano group to the formyl group using diisobutylaluminium hydride and optionally further reducing the formyl group to the group —CH$_2$OH using lithium aluminium hydride in tetrahydrofuran and subsequently proceeding in analogy to Scheme 5.

The aldehydes of formulae LXVI and LXVIII can also be obtained from the corresponding carboxylic acids by reaction with thionyl chloride and subsequent Rosenmund reduction.

The compounds of formula I can be used in the form of mixtures consisting of two or more compounds of formula I or in the form of mixtures with other liquid crystalline or non-liquid crystalline substances such as, for example, with substances from the classes of Schiff's bases, azobenzenes, azoxybenzenes, phenyl benzoates, cyclohexanecarboxylic acid phenyl esters, cyclohexanecarboxylic acid cyclohexyl esters, biphenyls, terphenyls, phenylcyclohexanes, cinnamic acid derivatives, phenylpyrimidines, diphenylpyrimidines, cyclohexylphenylpyrimidines, phenyldioxanes, 2-cyclohexyl-1-phenylethanes and the like. Such substances are known to a person skilled in the art or can be manufactured from known compounds by conventional techniques. Moreover, many of these compounds are commercially available.

The amount of the compounds of formula I in mixtures provided by the invention can, in general, be chosen according to desire. For example, the mixtures provided by the invention can consist of two or more compounds of formula I. The mixtures provided by the invention conveniently contain at least about 1 weight % of compounds of formula I.

Further, the mixtures provided by the invention can contain suitable optically active compounds (e.g. optically active biphenyls) and/or dichroic colouring substances (e.g. azo, azoxy and anthraquinone colouring substances). The amount of such compounds is determined by the solubility and the desired pitch, colour, extinction and the like. The amount of optically active compounds preferably amounts to about 4 weight % and the amount of dichroic colouring substance preferably amounts to at most about 10 weight %.

The manufacture of liquid crystalline mixtures and electro-optical devices containing one or more compounds of formula I can be carried out in a manner known per se.

The invention is also concerned with all novel compounds, mixtures, processes, uses and devices as described herein.

The following examples illustrate the manufacture of the inventive compounds. In the Examples, C denotes a crystalline phase, S denotes a smectic phase, N denotes a nematic phase, I denotes the isotropic phase and t.p. denotes a transition point between two different liquid crystalline phases. $\eta$ denotes the viscosity (bulk viscosity). Unless otherwise stated, percentages and ratios relating to solvent mixtures are expressed in volume, purity data determined by gas chromatography are expressed in area % and the remaining percentages and ratios are expressed in weight. Temperatures are in degrees Celsius (°C.), normal pressure is about 1 atmosphere and room temperature is about 23° C. The petroleum ether is a well-known mixture of low-boiling hydrocarbons. Unless indicated otherwise, the Examples were carried out as written.

EXAMPLE 1

A solution of 2.60 g of 4-(2,2-dibromovinyl)-4'-pentylbiphenyl in 50 ml of absolute tetrahydrofuran was placed at −78° C. in a sulphonation flask under argon gasification and treated within 5 minutes with 14.5 ml of a 1.2N solution of butyl lithium in hexane. After completion of the addition, the mixture was warmed to −10° C. within 10 minutes and then, after renewed cooling to −78° C., treated with a solution of 1.5 ml of phenyl cyanate in 10 ml of absolute tetrahydrofuran. The mixture was subsequently stirred at −78° C. for a further 30 minutes, then poured into 100 ml of water and extracted three times with 100 ml of diethyl ether each time. The organic phases were washed twice with 50 ml of water each time, dried over magnesium sulphate and concentrated. Low-pressure chromatography (0.5 bar) of the residue (2.51 g) on silica gel with hexane followed by 2% ethyl acetate/petroleum ether and subsequent recrystallization from methanol gave 1.02 g (58%) of (4'-pentyl-4-biphenylyl)propiolonitrile as colourless crystals (purity 99.6%); m.p. (C-N) 51.0° C., cl.p. (N-I) 120.2° C.

The 4-(2,2-dibromovinyl)-4'-pentylbiphenyl used as the starting material was prepared as follows:

(a) A solution of 6.23 g of 4'-pentyl-4-cyanobiphenyl in 50 ml of absolute toluene was placed at 0° C. in a sulphonation flask under argon gasification and treated within 10 minutes with 27 ml of a 1.36N solution of diisobutylaluminium hydride in toluene. After completion of the addition, the mixture was stirred at room temperature for a further 22 hours, then poured cautiously into 50 ml of 1N sulphuric acid and extracted three times with 100 ml of diethyl ether each time. The organic phases were washed once with 50 ml of 1N sulphuric acid and twice with 50 ml of water each time, dried over magnesium sulphate and concentrated. Low-pressure chromatography (0.5 bar) of the oily residue (6.0 g on silica gel with 10% ethyl acetate/petroleum ether gave 5.86 g (93%) of 4-formyl-4'-pentylbiphenyl as a colourless viscous oil (purity 99.7%).

(b) A solution of 15.3 g of tetrabromomethane in 150 ml of methylene chloride was placed at 0° C. in a sulphonation flask under argon gasification and treated within 5 minutes with a solution of 12.1 g of triphenylphosphine in 50 ml of methylene chloride. After completion of the addition, the clear orange reaction solution was stirred at 0° C. for a further 5 minutes and then a solution of 5.80 g of 4-formyl-4'-pentylbiphenyl in 50 ml of methylene chloride was added dropwise within 10 minutes. After stirring at 0° C. for a further 45 minutes, the yellow-orange mixture was poured into 1000 ml of hexane and the precipitate which thereby separated was filtered off (rinsing with hexane). The concentrated filtrate was digested with 400 ml of hexane, left to stand at 0° C. for 18 hours, filtered (rinsing with hexane) and the filtrate was concentrated. Low-pressure chromatography (0.5 bar) of the residue (9.8 g) on silica gel with hexane gave 5.15 g (55%) of 4-(2,2-dibromovinyl)-4'-pentylbiphenyl as colourless crystals (purity 99.1%); m.p. 95° C.

The following compounds can be manufactured in an analogous manner:
(4'-Propyl-4-biphenylyl)propiolonitrile,
(4'-butyl-4-biphenylyl)propiolonitrile,
(4'-hexyl-4-biphenylyl)propiolonitrile,
(4'-heptyl-4-biphenylyl)propiolonitrile,
(4'-ethoxy-4-biphenylyl)propiolonitrile,
(4'-propyloxy-4-biphenylyl)propiolonitrile,
(4'-butyloxy-4-biphenylyl)propiolonitrile,
(4'-pentyloxy-4-biphenylyl)propiolonitrile,
(4'-hexyloxy-4-biphenylyl)propiolonitrile.

EXAMPLE 2

In an analogous manner to Example 1, solution of 4-(2,2-dibromovinyl)-4'-pentylbiphenyl in absolute tetrahydrofuran was placed in a sulphonation flask and treated within 5 minutes with a solution of butyl lithium in hexane. After completion of the addition, the mixture was warmed to −10° C. within 10 minutes, then poured into water and extracted with diethyl ether. The organic phases were washed with water and saturated sodium chloride solution, dried over magnesium sulphate and concentrated. Low-pressure chromatography of the residue on silica gel with hexane and recrystallization from methanol gave 4-ethynyl-4′-pentylbiphenyl as colourless crystals (purity 99.5%); m.p. (C-N) 56.4° C., cl.p. (N-I) 82.7° C.

The following compounds can be manufactured in an analogous manner:
4-Ethynyl-4′-propylbiphenyl,
4-ethynyl-4′-butylbiphenyl,
4-ethynyl-4′-hexylbiphenyl,
4-ethynyl-4′-heptylbiphenyl,
4-ethynyl-4′-ethoxybiphenyl,
4-ethynyl-4′-propyloxybiphenyl,
4-ethynyl-4′-butyloxybiphenyl,
4-ethynyl-4′-pentyloxybiphenyl,
4-ethynyl-4′-hexyloxybiphenyl.

EXAMPLE 3

A solution of 7.88 g of $\beta,\beta$-dibromo-p-(trans-4-pentylcyclohexyl)styrene in 150 ml of absolute tetrahydrofuran was placed at −78° C. in a sulphonation flask under argon gasification and treated within 10 minutes with 63 ml of a 1.2N solution of butyl lithium in hexane. After completion of the addition, the mixture was stirred at −78° C. for a further 1 hour and at −10° C. for 1 hour, then poured into 100 ml of water and extracted three times with 100 ml of petroleum ether each time. The organic phases were washed with 100 ml of water and with 100 ml of saturated sodium chloride solution, dried over magnesium sulphate and concentrated. Low-pressure chromatography (0.5 bar) of the residual crystallizing oil on silica gel with hexane gave 4.13 g (85%) of 1-ethynyl-4-(trans-4-pentylcyclohexyl)-benzene as colourless crystals (purity 99.3%); m.p. (C-N) 39.4° C., cl.p. 42.1° C.

The $\beta,\beta$-dibromo-p-(trans-4-pentylcyclohexyl)styrene used as the starting material was prepared as follows:

A solution of 16.6 g of tetrabromomethane in 230 ml of methylene chloride was placed at 0° C. in a sulphonation flask under an argon atmosphere and treated portionwise within 10 minutes with 26.2 g of solid triphenylphosphine; there thereby resulted a clear, deep orange solution. After completion of the addition, the mixture was stirred at 0° C. for a further 5 minutes and then a solution of 6.46 g of p-(trans-4-pentylcyclohexyl)benzaldehyde in 20 ml of methylene chloride was added dropwise within 10 minutes. After stirring at 0° C. for a further 1 hour, the orange mixture was poured into 750 ml of hexane and the precipitate which thereby separated was filtered off (rinsing with hexane). The concentrated filtrate (20.4 g) was digested with 250 ml of warm hexane, filtered (rinsing with warm hexane) and the filtrate was concentrated. Low-pressure chromatography (0.5 bar) of the residual oil (9.70 g) on silica gel with 3% ethyl acetate/petroleum ether gave 8.08 g (78%) of $\beta,\beta$-dibromo-p-(trans-4-pentylcyclohexyl)styrene as colourless crystals (purity 97.5%); m.p. 48° C.

The following compounds can be manufactured in an analogous manner:
1-Ethynyl-4-(trans-4-propylcyclohexyl)benzene, m.p. 39.9° C.,
1-ethynyl-4-(trans-4-butylcyclohexyl)benzene,
1-ethynyl-4-(trans-4-hexylcyclohexyl)benzene,
1-ethynyl-4-(trans-4-heptylcyclohexyl)benzene, m.p. (C-N) 37.6° C., cl.p. (N-I) 47.5° C.

EXAMPLE 4

A solution of 1.2 g of 1-ethynyl-4-(trans-4-pentylcyclohexyl)benzene (prepared according to Example 3) in 50 ml of absolute tetrahydrofuran was placed at −40° C. in a sulphonation flask under argon gasification and treated with 4.72 ml of a 1.2N solution of butyl lithium in hexane. After completion of the addition, the mixture was stirred at −40° C. for a further 15 minutes, subsequently treated at −78° C. with 1.07 ml of phenyl cyanate and stirred at −78° C. for a further 45 minutes. The mixture was then poured into 50 ml of water and extracted three times with 50 ml of diethyl ether each time. The organic phases were washed with 50 ml of water and 50 ml of saturated sodium chloride solution, dried over magnesium sulphate and concentrated. Low-pressure chromatography (0.5 bar) of the crystalline residue on silica gel with 3% ethyl acetate/petroleum ether gave 1.20 g (91%) of p-(trans-4-pentylcyclohexyl)phenylpropiolonitrile as colourless crystals (purity 99.6%). A single crystallization from 50 ml of methanol yielded 687 mg of the product with m.p. (C-N) 49.7° C. and cl.p. (N-I) 128.9° C.

The following compounds can be manufactured in an analogous manner:
p-(Trans-4-propylcyclohexyl)phenylpropiolonitrile,
p-(trans-4-butylcyclohexyl)phenylpropiolonitrile,
p-(trans-4-hexylcyclohexyl)phenylpropiolonitrile,
p-(trans-4-heptylcyclohexyl)phenylpropiolonitrile.

EXAMPLE 5

A solution of 1.55 g of $\beta,\beta$-dibromo-p-[2-(trans-4-pentylcyclohexyl)ethyl]styrene in 35 ml of absolute tetrahydrofuran was placed at about −45° C. in a sulphonation flask under argon gasification and treated within 5 minutes with 8.8 ml of a 1.2N solution of butyl lithium in hexane. After completion of the addition, the mixture was stirred at the same temperature for a further 90 minutes, then cooled to −78° C. and treated with 0.79 ml of phenyl cyanate. The mixture was subsequently stirred at −78° C. for a further 3 hours, then poured into 50 ml of 1N sodium hydroxide and extracted three times with 50 ml of diethyl ether/petroleum ether (1:1) each time. The organic phases were washed with 50 ml of 1N sodium hydroxide and 50 ml of saturated sodium chloride solution, dried over magnesium sulphate and concentrated. Low-pressure chromatography (0.5 bar) of the residue (1.17 g) on silica gel with hexane followed by 3% ethyl acetate/petroleum ether gave 740 mg (69%) of p-[2-(trans-4-pentylcyclohexyl)ethyl]phenylpropiolonitrile as colourless crystals (purity 97.3%) which were recrystallized further from methanol; m.p. (C-N) 36.7° C., cl.p. (N-I) 105.5° C.

The $\beta,\beta$-dibromo-p-[2-(trans-4-pentylcyclohexyl)ethyl]styrene used as the starting material was prepared as follows:

(a) A solution of 7.08 g of p-[2-(trans-4-pentylcyclohexyl)ethyl]benzonitrile in 50 ml of absolute toluene was placed at 0° C. in a sulphonation flask under argon gasification and treated within 15 minutes with 29 ml of a 1.21N solution of diisobutylaluminium hydride in toluene in such a manner that the internal temperature did not exceed 5° C. After completion of the addition, the mixture was stirred at room temperature for a further 2 hours, then treated cautiously with 50 ml of 0.5N sulphuric acid and extracted three times with 100 ml of diethyl ether each time. The organic phases were washed twice with 50 ml of semi-saturated sodium chloride solution each time, dried over magnesium sulphate and concentrated. There were obtained 6.20 g (87%) of p-[2-(trans-4-pentylcyclohexyl)ethyl]benzaldehyde as a colourless viscous oil (purity 97%) which was used without additional purification.

(b) A mixture of 13.27 g of tetrabromomethane, 10.49 g of triphenylphosphine and 2.62 g of zinc dust in 100 ml of methylene chloride was stirred at room temperature for 24 hours in a sulphonation flask under argon gasification. In so doing, the heterogeneous mixture changed in colour via yellow-green to dark violet and pale violet. A solution of 2.86 g of p-[2-(trans-4-pentylcyclohexyl)ethyl]benzaldehyde in 10 ml of methylene chloride was subsequently added dropwise, the mixture was stirred at room temperature for 4 hours and then poured into 700 ml of pentane. The voluminous precipitate which separated was filtered off (rinsing with pentane), the concentrated filtrate (5.25 g) was digested with 300 ml of pentane, filtered and concentrated. Low-pressure chromatography (0.5 bar) of the residue (4.8 g) on silica gel with 3% ethyl acetate/petroleum ether gave 3.13 g (71%) of $\beta,\beta$-dibromo-p-[2-(trans-4-pentylcyclohexyl)ethyl]styrene as colourless crystals (purity 99.8%); m.p. 47.3° C.

The following compounds can be manufactured in an analogous manner:

p-[2-(Trans-4-propylcyclohexyl)ethyl]phenylpropiolonitrile,
p-[2-(trans-4-butylcyclohexyl)ethyl]phenylpropiolonitrile,
p-[2-(trans-4-hexylcyclohexyl)ethyl]phenylpropiolonitrile,
p-[2-(trans-4-heptylcyclohexyl)ethyl]phenylpropiolonitrile,

EXAMPLE 6

In an analogous manner to Example 5, a solution of $\beta,\beta$-dibromo-p-[2-(trans-4-pentylcyclohexyl)ethyl]styrene in absolute tetrahydrofuran was placed in a sulphonation flask and treated within 5 minutes with a solution of butyl lithium in hexane. After completion of the addition, the mixture was stirred at the same temperature for a further 90 minutes, then poured into 1N sodium hydroxide and extracted with petroleum ether. The organic phases were washed with water and saturated sodium chloride solution, dried over magnesium sulphate and concentrated. Low-pressure chromatography of the residue on silica gel with hexane gave pure 1-ethynyl-4-[2-(trans-4-pentylcyclohexyl)ethyl]benzene as colourless crystals; m.p. (C-N) 25.5° C., cl.p. 42.5° C.

The following compounds can be manufactured in an analogous manner:

1-Ethynyl-4-[2-(trans-4-propylcyclohexyl)ethyl]benzene,
1-ethynyl-4-[2-(trans-4-butylcyclohexyl)ethyl]benzene, m.p. (C-N) 10.0° C., cl.p. (N-I) 25.2° C., $\eta(22°$ C.) = 13.5 cp,
1-ethynyl-4-[2-(trans-4-hexylcyclohexyl)ethyl]benzene,
1-ethynyl-4-[2-(trans-4-heptylcyclohexyl)ethyl]benzene, m.p. (C-N) 29.9° C., cl.p. (N-I) 49.3° C.

EXAMPLE 7

A solution of 3.5 g of trans-2-[p-(2,2-dibromovinyl)phenyl]-5-butyl-1,3-dioxane in 80 ml of absolute tetrahydrofuran was placed at −78° C. in a sulphonation flask under argon gasification and treated within 5 minutes with 13.4 ml of a 1.2N solution of butyl lithium in hexane. After completion of the addition, the mixture was held at −10° C. for 1 hour, then again cooled to −78° C. and treated with 1.2 ml of phenyl cyanate within 5 minutes. The mixture was stirred at −78° C. for a further 30 minutes, then poured into 100 ml of water and extracted three times with 100 ml of diethyl ether each time. The organic phases were washed with 100 ml of water and 100 ml of saturated sodium chloride solution, dried over potassium carbonate and concentrated. Low-pressure chromatography (0.5 bar) of the residue (3.26 g) on silica gel with petroleum ether/ethyl acetate/triethylamine (97:3:0.2) gave 1.18 g (50%) of p-(trans-5-butyl-1,3-dioxan-2-yl)phenylpropiolonitrile (purity 98.7%). A recrystallization from 50 ml of hexane yielded 1.03 g of the nitrile as colourless crystals (purity 99.7%); m.p. (C-N) 54.3° C., cl.p. (N-I) 108.7° C.

The trans-2-[p-(2,2-dibromovinyl)phenyl]-5-butyl-1,3-dioxane used as the starting material was prepared as follows:

(a) A solution of 4.91 g of p-(trans-5-butyl-1,3-dioxan-2-yl)benzonitrile in 50 ml of absolute toluene was placed at 0° C. in a sulphonation flask under argon gasification and treated within 3 minutes with 10 ml of a 3N solution of diisobutylaluminum hydride in toluene. After completion of the addition, the mixture was stirred at room temperature for a further 22 hours, then poured cautiously into 100 ml of 10% potassium sodium tartrate solution and extracted three times with 100 ml of diethyl ether each time. The organic phased were washed with 100 ml of 10% potassium sodium tartrate solution and once with 100 ml of saturated sodium chloride solution, dried over potassium carbonate and concentrated. Low-pressure chromatography (0.5 bar) of the residue (5.5 g) on silica gel with petroleum ether/ethyl acetate/triethylamine (80:20:1) gave 5.08 g of p-(trans-5-butyl-1,3-dioxan-2-yl)benzaldehyde as a colourless viscous oil (purity 98.3%) which was used without additional purification.

(b) A solution of 13.6 g of tetrabromomethane in 150 ml of methylene chloride was placed at 0° C. in a sulphonation flask under argon gasification and treated within 10 minutes with a solution of 21.51 g of triphenylphosphine in 40 ml of methylene chloride. After completion of the addition, the clear orange solution was stirred at 0° C. for a further 5 minutes and then a solution of 5.08 g of p-(trans-5-butyl-1,3-dioxan-2-yl)benzaldehyde in 30 ml of methylene chloride was added dropwise within 5 minutes. The mixture was subsequently stirred at 0° C. for a further 30 minutes, then the flask content was poured into 800 ml of hexane and the separated precipitate was filtered off (rinsing with hexane). The concentrated filtrate was digested with 400 ml of hexane, left to stand at 0° C. for 15 hours, filtered (rinsing with hexane) and the filtrate was concentrated. Low-pressure chromatography (0.5 bar) of the residue (8.2 g) on silica gel with hexane followed by petroleum ether/ethyl acetate/triethylamine (97:3:0.5) gave 3.23 g of trans-2-[p-(2,2-dibromovinyl)phenyl]-5-butyl-1,3-dioxane as colourless crystals (purity 95.1%).

The following compounds can be manufactured in an analogous manner:

p-(Trans-5-propyl-1,3-dioxan-2-yl)phenylpropiolonitrile,
p-(trans-5-pentyl-1,3-dioxan-2-yl)phenylpropiolonitrile; m.p. (C-N) 60.3° C., cl.p. (N-I) 111.0° C., p-(trans-5-hexyl-1,3-dioxan-2-yl)phenylpropiolonitrile,
p-(trans-5-heptyl-1,3-dioxan-2-yl)phenylpropiolonitrile.

EXAMPLE 8

About 100 ml of ammonia were condensed at −78° C. under argon gasification in a sulphonation flask equipped with a gas inlet tube, dry-ice condenser and mechanical stirrer and treated with sodium metal until the blue colouration persisted. A spatula tip of iron (III) nitrate was subsequently added, the now greyish mixture was treated portionwise with 820 mg of sodium metal and the resulting mixture was stirred at −78° C. for a further 30 minutes. A solution of 1.02 g of 2-[p-(2,2-dibromovinyl)phenyl]-5-pentylpyrimidine in 10 ml of diethyl ether was added dropwise within 5 minutes, then the green-yellow mixture was stirred at −78° C. for a further 45 minutes, the ammonia was evaporated and the mixture was subsequently treated with 30 ml of saturated ammonium chloride solution and extracted three times with 50 ml of diethyl ether each time. The organic phases were washed twice with 50 ml of water each time and once with saturated sodium chloride solution, dried over magnesium sulphate and concentrated. Low-pressure chromatography (0.5 bar) of the resulting orange oil on silica gel with 10% ethyl acetate/petroleum ether gave 447 mg (71%) of 2-(p-ethynylphenyl)-5-pentylpyrimidine as colourless crystals; m.p. 72.3° C.

The 2-[p-(2,2-dibromovinyl)phenyl]-5-pentylpyrimidine used as the starting material was prepared as follows:

(a) A solution of 3.50 g of p-(5-pentyl-2-pyrimidinyl)benzonitrile in 120 ml of methylene chloride was placed at −78° C. under argon gasification in a sulphonation flask equipped with a mechanical stirrer and treated within 5 minutes with 14 ml of a 1.5N solution of diisobutylaluminium hydride in toluene (in so doing a yellow colouration resulted and shortly before the end of the addition a white precipitate formed). The mixture was stirred at −78° C. for a further 30 minutes, then poured into 100 ml of 1N hydrochloric acid and extracted three times with 150 ml of diethyl ether each time. The organic phases were washed twice with 100 ml of water each time and once with 100 ml of saturated sodium chloride solution, dried over magnesium sulphate and concentrated. Low-pressure chromatography (0.5 bar) of the residue (2.3 g) on silica gel with 10% ethyl acetate/petroleum ether gave 2.08 g (59%) of p-(5-pentyl-2-pyrimidinyl)benzaldehyde as colourless crystals which were used without additional purification.

(b) A solution of 5.44 g of tetrabromomethane in 80 ml of methylene chloride was placed at 0° C. under argon gasification in a sulphonation flask equipped with a mechanical stirrer and treated within 10 minutes with a solution of 8.6 g of triphenylphosphine in 20 ml of methylene chloride. After completion of the addition, the clear orange solution was stirred at 0° C. for a further 5 minutes and then a solution of 2.08 g of p-(5-pentyl-2-pyrimidinyl)benzaldehyde in 15 ml of methylene chloride was added dropwise within 5 minutes. The mixture was subsequently stirred at 0° C. for a further 30 minutes, then the flask content was poured into 700 ml of hexane and the precipitate which thereby separated was filtered off (rinsing with hexane). The concentrated filtrate was digested with 200 ml of hexane, left to stand at 0° C. for 18 hours, filtered (rinsing with hexane) and the filtrate was concentrated. Low-pressure chromatography (0.5 bar) of the residue (3.7 g) on silica gel with 3% ethyl acetate/petroleum ether gave 2.70 g (80%) of 2-[p-(2,2-dibromovinyl)phenyl]-5-pentylpyrimidine as colourless crystals (purity 94.5%); m.p. 74° C.

The following compounds can be manufactured in an analogous manner:
2-(p-Ethynylphenyl)-5-propylpyrimidine,
2-(p-ethynylphenyl)-5-butylpyrimidine,
2-(p-ethynylphenyl)-5-hexylpyrimidine,
2-(p-ethynylphenyl)-5-heptylpyrimidine,
2-(p-ethynylphenyl)-5-ethoxypyrimidine,
2-(p-ethynylphenyl)-5-propyloxypyrimidine,
2-(p-ethynylphenyl)-5-butyloxypyrimidine,
2-(p-ethynylphenyl)-5-pentyloxypyrimidine,
2-(p-ethynylphenyl)-5-hexyloxypyrimidine.

EXAMPLE 9

A solution of 355 mg of 2-(p-ethynylphenyl)-5-pentylpyrimidine (prepared according to Example 8) in 30 ml of absolute tetrahydrofuran was placed at −78° C. in a sulphonation flask under argon gasification and treated within 15 minutes with a solution, cooled to about 0° C., of 152 mg of lithium diisopropylamide (prepared by adding 0.89 ml of a 1.60N solution of butyl lithium in hexane to a solution of 0.22 ml of diisopropylamine in 10 ml of absolute tetrahydrofuran at 0° C.) in 10 ml of absolute tetrahydrofuran. After 5 minutes, 182 µl of phenyl cyanate were added, the mixture was stirred at −78° C. for 90 minutes, then poured into 30 ml of water and extracted three times with 50 ml of diethyl ether each time. The organic phases were washed with 50 ml of saturated sodium chloride solution, dried over magnesium sulphate and concentrated. Low-pressure chromatography (0.4 bar) of the residue on silica gel with 5% ethyl acetate/petroleum ether gave 88 mg (22%) of p-(5-pentyl-2-pyrimidinyl)phenylpropiolonitrile as colourless crystals. Recrystallization from methanol yielded colourless needles (purity 99.4%); m.p. (C-N) 76.2° C., cl.p. (N-I) 128.5° C.

The following compounds can be manufactured in an analogous manner:
p-(5-Propyl-2-pyrimidinyl)phenylpropiolonitrile,
p-(5-butyl-2-pyrimidinyl)phenylpropiolonitrile,
p-(5-hexyl-2-pyrimidinyl)phenylpropiolonitrile,
p-(5-heptyl-2-pyrimidinyl)phenylpropiolonitrile,
p-(5-ethoxy-2-pyrimidinyl)phenylpropiolonitrile,
p-(5-propyloxy-2-pyrimidinyl)phenylpropiolonitrile,
p-(5-butyloxy-2-pyrimidinyl)phenylpropiolonitrile,
p-(5-pentyloxy-2-pyrimidinyl)phenylpropiolonitrile,
p-(5-hexyloxy-2-pyrimidinyl)phenylpropiolonitrile.

EXAMPLE 10

A mixture of 143 mg of (p-hydroxyphenyl)propiolonitrile, 218 mg of trans-4-pentylcyclohexanecarboxylic acid, 227 mg of N,N'-dicyclohexylcarbodiimide and 12.2 mg of 4-(dimethylamino)pyridine in 15 ml of methylene chloride was stirred at room temperature for 105 minutes in a round flask under argon gasification. The yellow heterogeneous mixture was subsequently poured into 30 ml of water and extracted twice with 30 ml of methylene chloride each time. The organic phases were washed in sequence twice with 30 ml of water each time, twice with 30 ml of 5% acetic acid each time and twice with 30 ml of water each time, dried over magnesium sulphate and concentrated. Low-pressure chromatography (0.4 bar) of the residue (383 mg) on silica gel with 3% ethyl acetate/petroleum ether gave 270 mg (84%) of trans-4-pentylcyclohexanecarboxylic acid p-(2-cyanoethynyl)phenyl ester as colourless crystals. A single crystallization from hexane yielded 219 mg of the ester as colourless platelets (purity 99.7%); m.p. (C-N) 76.8° C., cl.p. (N-I) 153.2° C.

The (p-hydroxyphenyl)propiolonitrile used as the starting material was prepared as follows:

(a) A mixture of 4.40 g of 4-iodophenol, 2.36 g of ethynyl-trimethylsilane, 280 mg of bis-(triphenylphosphine)-palladium (II) dichloride and 20 mg of anhydrous copper (I) iodide in 80 ml of triethylamine was stirred at 50° C. for 4 hours under argon gasification in a sulphonation flask equipped with a mechanical stirrer. The resulting grey-brown heterogeneous mixture was filtered (rinsing with diethyl ether) and the filtrate was concentrated. Low-pressure chromatography (0.5 bar) of the residual brown-orange oil (5.89 g) on silica gel with 30% ethyl acetate/petroleum ether gave 4.40 g of orange oil which, after additional bulb-tube distillation (135°-160° C./0.4-0.3 mmHg), yielded 3.25 g (86%) of p-[(trimethylsilyl)ethynyl]phenol as light yellowish wax-like crystals; m.p. 60°-63.5° C.

(b) A solution of 381 mg of p-[(trimethylsilyl)ethynyl]phenol in 5 ml of hexamethylphosphoric acid triamide was treated at −5° C. in a sulphonation flask under argon gasification with 2.5 ml of a 1.75M solution of methyl lithium in diethyl ether. 15 minutes after completion of the addition the mixture, which had become a red slurry, was diluted with 5 ml of absolute tetrahydrofuran and subsequently stirred at room temperature for 3 hours. The mixture was then cooled to −30° C. and 322 μl of phenyl cyanate were added. The new brown-orange clear solution was warmed to 0° C. within 60 minutes, then poured into 50 ml of 1N hydrochloric acid and extracted three times with 50 ml of diethyl ether each time. The organic phases were washed a further three times with 50 ml of water each time (to which was added a small amount of sodium chloride solution), dried over magnesium sulphate and concentrated. Low-pressure chromatography (0.4 bar) of the orange residue (570 mg) on silica gel with 15% ethyl acetate/petroleum ether followed by 20% ethyl acetate/petroleum ether gave 160 mg (56%) of (p-hydroxyphenyl)propiolonitrile as light yellowish crystals; m.p. 134°-137° C.

The following compounds can be manufactured in an analogous manner:

Trans-4-propylcyclohexanecarboxylic acid p-(2-cyanoethynyl)phenyl ester,
trans-4-butylcyclohexanecarboxylic acid p-(2-cyanoethynyl)phenyl ester,
trans-4-hexylcyclohexanecarboxylic acid p-(2-cyanoethynyl)phenyl ester,
trans-4-heptylcyclohexanecarboxylic acid p-(2-cyanoethynyl)phenyl ester,
p-propylbenzoic acid p'-(2-cyanoethynyl)phenyl ester,
p-butylbenzoic acid p'-(2-cyanoethynyl)phenyl ester,
p-pentylbenzoic acid p'-(2-cyanoethynyl)phenyl ester,
p-hexylbenzoic acid p'-(2-cyanoethynyl)phenyl ester,
p-heptylbenzoic acid p'-(2-cyanoethynyl)phenyl ester,
p-ethoxybenzoic acid p'-(2-cyanoethynyl)phenyl ester,
p-propyloxybenzoic acid p'-(2-cyanoethynyl)phenyl ester,
p-butyloxybenzoic acid p'-(2-cyanoethynyl)phenyl ester,
p-pentyloxybenzoic acid p'-(2-cyanoethynyl)phenyl ester,
p-hexyloxybenzoic acid p'-(2-cyanoethynyl)phenyl ester.

EXAMPLE 11

A solution of 382 mg of p-[(trimethylsilyl)ethynyl]phenol (prepared according to Example 10) in 15 ml of a 1:1 mixture of methanol and 1N aqueous potassium hydroxide solution was stirred at room temperature for 45 minutes in a round flask under argon gasification. Methanol was subsequently removed on a rotary evaporator and the residue, after the addition of 30 ml of 1N hydrochloric acid, was extracted three times with 30 ml of diethyl ether each time. The organic phases were washed twice with 30 ml of water each time and once with 30 ml of saturated sodium chloride solution, dried over magnesium sulphate and concentrated. There were obtained 207 mg (88%) of p-ethynylphenol as a colourless oil (decomposing rapidly in the pure state) which was taken up immediately in 50 ml of diethyl ether and treated with 436 mg of trans-4-pentylcyclohexanecarboxylic acid, 454 mg of N,N'-dicyclohexylcarbodiimide and 24.4 mg of 4-(dimethylamino)pyridine. This mixture was stirred at room temperature for 18 hours and subsequently filtered. The filtrate was treated with 50 ml of water and extracted three times with 50 ml of diethyl ether each time. The organic phases were washed with 50 ml of water and with 50 ml of saturated sodium chloride solution, dried over magnesium sulphate and concentrated. Low-pressure chromatography (0.4 bar) of the residue (847 mg) on silica gel with 3% ethyl acetate petroleum ether gave 277 mg (46%) of trans-4-pentylcyclohexanecarboxylic acid p-ethynylphenyl ester as colourless crystals (purity 98.5%) which were recrystallized further from methanol (purity 99.1%); m.p. (C-N) 50.6° C., cl.p. (N-I) 78.5° C.

The following compounds can be manufactured in an analogous manner:

Trans-4-propylcyclohexanecarboxylic acid p-ethynylphenyl ester,
trans-4-butylcyclohexanecarboxylic acid p-ethynylphenyl ester,
trans-4-hexylcyclohexanecarboxylic acid p-ethynylphenyl ester,
trans-4-heptylcyclohexanecarboxylic acid p-ethynylphenyl ester,
p-propylbenzoic acid p'-ethynylphenyl ester,
p-butylbenzoic acid p'-ethynylphenyl ester,
p-pentylbenzoic acid p'-ethynylphenyl ester,
p-hexylbenzoic acid p'-ethynylphenyl ester,
p-heptylbenzoic acid p'-ethynylphenyl ester,
p-ethoxybenzoic acid p'-ethynylphenyl ester,
p-propyloxybenzoic acid p'-ethynylphenyl ester,
p-butyloxybenzoic acid p'-ethynylphenyl ester,
p-pentyloxybenzoic acid p'-ethynylphenyl ester,
p-hexyloxybenzoic acid p'-ethynylphenyl ester,
p-heptyloxybenzoic acid p'-ethynylphenyl ester.

EXAMPLE 12

A solution of 480 mg of 1-[trans-4-(2,2-dibromovinyl)cyclohexyl]-4-pentylbenzene in 60 ml of absolute tetrahydrofuran was placed at −78° C. in a sulphonation flask under argon gasification and treated within 3 minutes with 3.2 ml of a 0.1N solution of butyl lithium in hexane. After completion of the addition, the mixture was stirred at −78° C. for a further 2.5 hours, then poured into 150 ml of water and extracted three times with 150 ml of petroleum ether each time. The organic phases were washed with 100 ml of water, dried over magnesium sulphate and concentrated. Low-pressure chromatography (0.5 bar) of the residue (310 mg) on silica gel with hexane gave 255 mg (83.5%) of 1-(trans-4-ethynylcyclohexyl)-4-pentylbenzene as a colourless oil (purity 95.9%).

The 1-[trans-4-(2,2-dibromovinyl)cyclohexyl]-4-pentylbenzene used as the starting material was prepared as follows:

(a) A solution of 2.0 g of trans-4-(p-pentylphenyl)cyclohexanecarbonitrile in 60 ml of methylene chloride was placed at −78° C. under argon gasification in a sulphonation flask equipped with a mechanical stirrer and treated within 3 minutes with 13.2 ml of a 1.5M solution of diisobutylaluminium hydride in toluene. The mixture was subsequently stirred for a further 2 hours with gradual warming to room temperature, then poured cautiously into 100 ml of 10% potassium sodium tartrate solution and extracted three times with 200 ml of diethyl ether each time. The organic phases were washed twice with 100 ml of water each time, dried over potassium carbonate and concentrated. There were obtained 1.98 g of trans-4-(p-pentylphenyl)cyclohexanecarboxaldehyde (purity 86.1%) as a viscous oil which was used without additional purification.

(b) A solution of 5.0 g of tetrabromomethane in 60 ml of methylene chloride was placed a −10° C. in a sulphonation flask under argon gasification and treated within 5 minutes with a solution of 7.9 g of triphenylphosphine in 20 ml of methylene chloride. The resulting clear orange solution was stirred at −10° C. for a further 1 minute and then a solution of 1.95 g of trans-4-(p-pentylphenyl)cyclohexanecarboxaldehyde in 20 ml of methylene chloride was added dropwise within 3 minutes. The mixture was subsequently left to stand at −18° C. overnight, then poured into 600 ml of hexane and the separated precipitate was filtered off (rinsing with hexane). The concentrated filtrate was digested with 300 ml of hexane, left to stand at −18° C. for 30 minutes, filtered (rinsing with hexane) and the filtrate was concetrated. Low-pressure chromatography (0.5 bar) of the residue (1.87 g) on silica gel with hexane gave 503 mg of 1-[trans-4-(2,2-dibromovinyl)cyclohexyl]-4-pentylbenzene as colourless crystals (purity 95.8%); m.p. 35°-37.7° C.

The following compounds can be manufactured in an analogous manner:

1-(Trans-4-ethynylcyclohexyl)-4-propylbenzene,
1-(trans-4-ethynylcyclohexyl)-4-butylbenzene,
1-(trans-4-ethynylcyclohexyl)-4-hexylbenzene,
1-(trans-4-ethynylcyclohexyl)-4-heptylbenzene,
1-(trans-4-ethynylcyclohexyl)-4-ethoxybenzene,
1(trans-4-ethynylcyclohexyl)-4-propyloxybenzene,
1-(trans-4-ethynylcyclohexyl)-4-butyloxybenzene,
1-(trans-4-ethynylcyclohexyl)-4-pentyloxybenzene,
1-(trans-4-ethynylcyclohexyl)-4-hexyloxybenzene,
trans-1-(trans-4-ethynylcyclohexyl)-4-propylcyclohexane,
trans-1-(trans-4-ethynylcyclohexyl)-4-butylcyclohexane,
trans-1-(trans-4-ethynylcyclohexyl)-4-pentylcyclohexane,
trans-1-(trans-4-ethynylcyclohexyl)-4-hexylcyclohexane,
trans-1-(trans-4-ethynylcyclohexyl)-4-heptylcyclohexane.

EXAMPLE 13

A solution of 254 mg of 1-(trans-4-ethynylcyclohexyl)-4-pentylbenzene (prepared according to Example 12) in 60 ml of absolute tetrahydrofuran was placed at −45° C. in a 100 ml sulphonation flask under argon gasification and treated within 1 minute with 1.2 ml of a 1.0N solution of butyl lithium in hexane. After completion of the addition, the mixture was stirred at −45° C. for a further 15 minutes, then cooled to −78° C. and treated with 182 μl of phenyl cyanate. The mixture was stirred at −78° C. for a further 90 minutes, then poured into 200 ml of water and extracted three times with 100 ml of diethyl ether each time. The organic phases were washed a further twice with 100 ml of water each time and once with 100 ml of saturated sodium chloride solution, dried over magnesium sulphate and concentrated. Low-pressure chromatography (0.5 bar) of the residue (380 mg) on silica gel with 2% ethyl acetate/petroleum ether gave 186 mg (66.6%) of trans-4-(p-pentylphenyl)cyclohexanepropiolonitrile as colourless crystals (purity 97.3%) which were recrystallized further from hexane (purity 99.3%); m.p. (C-I) 46.9° C., cl.p. (N-I) 45.4° C.

The following compounds can be manufactured in an analogous manner:

Trans-4-(p-propylphenyl)cyclohexanepropiolonitrile,
trans-4-(p-butylphenyl)cyclohexanepropiolonitrile,
trans-4-(p-hexylphenyl)cyclohexanepropiolonitrile,
trans-4-(p-heptylphenyl)cyclohexanepropiolonitrile,
trans-4-(p-ethoxyphenyl)cyclohexanepropiolinitrile,
trans-4-(p-propyloxyphenyl)cyclohexanepropiolonitrile,
trans-4-(p-butyloxyphenyl)cyclohexanepropiolonitrile,
trans-4-(p-pentyloxyphenyl)cyclohexanepropiolonitrile,
trans-4-(p-hexyloxyphenyl)cyclohexanepropiolonitrile,
trans-4-(trans-4-propylcyclohexyl)cyclohexanepropiolonitrile,
trans-4-(trans-4-butylcyclohexyl)cyclohexanepropiolonitrile,
trans-4-(trans-4-pentylcyclohexyl)cyclohexanepropiolonitrile,
trans-4-(trans-4-hexylcyclohexyl)cyclohexanepropiolonitrile,
trans-4-(trans-4-heptylcyclohexyl)cyclohexanepropiolonitrile.

EXAMPLE 14

A solution of 2.66 g of trans-1-(2,2-dibromovinyl)-4-[2-(trans-4-pentylcyclohexyl)ethyl]cyclohexane in 120 ml of absolute tetrahydrofuran was placed at −78° C. in a sulphonation flask under argon gasification and treated within 10 minutes with 15.2 ml of a 0.1N solution of butyl lithium in hexane. After completion of the addition, the mixture was stirred at −78° C. for a further 2 hours, then poured into 100 ml of water and extracted three times with 100 ml of petroleum ether each time. The organic phases were washed twice with 50 ml of water each time and once with 50 ml of saturated sodium chloride solution, dried over magnesium sulphate and concentrated. Low-pressure chromatography (0.5 bar) of the residue (1.90 g) on silica gel with hexane gave 1.48 g (88%) of trans-1-ethynyl-4-[2-(trans-4-pentylcyclohexyl)ethyl]cyclohexane as a trans/cis epimer mixture (about 9:1). Fractional crystallization from 50 ml of methanol yielded 883 mg of pure trans-1-ethynyl-4-[2-(trans-4-pentylcyclohexyl)ethyl]cyclohexane as colourless crystals; m.p. (C-N) 51.3° C., cl.p. (N-I) 68.0° C.

The trans-1-(2,2-dibromovinyl)-4-[2-(trans-4-pentylcyclohexyl)ethyl]cyclohexane used as the starting material was prepared as follows:

(a) A solution of 2.3 g of trans-4-[2-(trans-4-pentylcyclohexyl)ethyl]cyclohexanecarbonitrile in 100 ml of methylene chloride was placed at −78° C. in a sulphonation flask under argon gasification and treated within 3 minutes with 10.5 ml of a 1.5M solution of diisobutylaluminium hydride in toluene. The mixture was subsequently stirred at −78° C. for a further 4 hours, then treated cautiously with 50 ml of 10% potassium sodium tartrate solution and extracted three times with 100 ml of diethyl ether each time. The organic phases were washed twice with 50 ml of water each time and once with 50 ml of saturated sodium chloride solution, dried over magnesium sulphate and concentrated. Low-pressure chromatography (0.5 bar) of the residue (2.1 g) on silica gel with 5% ethyl acetate/petroleum ether gave 1.95 g (84.4%) of trans-4-[2-(trans-4-pentylcyclohexyl)ethyl]cyclohexanecarboxaldehyde which contained about 10% of the corresponding epimeric cis aldehyde in accordance with NMR spectroscopic analysis and which was reacted without additional purification.

(b) A solution of 4.4 g of tetrabromomethane in 80 ml of methylene chloride was placed at −15° C. in a sulphonation flask under argon gasification and treated within 5 minutes with a solution of 7.0 g of triphenylphosphine in 20 ml of methylene chloride. The clear deep orange solution was stirred at −5° C. for a further 10 minutes and then a solution of 1.95 g of the trans-4-[2-(trans-4-pentylcyclohexyl)ethyl]cyclohexanecarboxaldehyde in 20 ml of methylene chloride was added dropwise within 10 minutes. The mixture was stirred at 0° C. for a further 30 minutes, then poured into 600 ml of hexane and the precipitate which thereby separated was filtered off (rinsing with hexane). The concentrated filtrate was digested with 300 ml of hexane, left to stand at 0° C. for 30 minutes, filtered (rinsing with hexane) and the filtrate was concentrated. Low-pressure chromatography (0.5 bar) of the residue (3.0 g) on silica gel with hexane gave 2.68 g (89.2%) of trans-1-(2,2-dibromovinyl)-4-[2-(trans-4-pentylcyclohexyl)ethyl]cyclohexane which contained about 10% of the corresponding epimeric cis compound in accordance with NMR spectroscopic analysis and which was used without additional purification.

The following compounds can be manufactured in an analogous manner:

Trans-1-ethynyl-4-[2-(trans-4-propylcyclohexyl)ethyl]cyclohexane, trans-1-ethynyl-4-[2-(trans-4-butylcyclohexyl)ethyl]cyclohexane, trans-1-ethynyl-4-[2-(trans-4-hexylcyclohexyl)ethyl]cyclohexane, trans-1-ethynyl-4-[2-(trans-4-heptylcyclohexyl)ethyl]cyclohexane, 1-propyl-4-[2-(trans-4-ethynylcyclohexyl)ethyl]benzene, 1-butyl-4-[2-(trans-4-ethynylcyclohexyl)ethyl]benzene, 1-pentyl-4-[2-(trans-4-ethynylcyclohexyl)ethyl]benzene, 1-hexyl-4-[2-(trans-4-ethynylcyclohexyl)ethyl]benzene, 1-heptyl-4-[2-(trans-4-ethynylcyclohexyl)ethyl]benzene, 1-ethoxy-4-[2-(trans-4-ethynylcyclohexyl)ethyl]benzene, 1-propyloxy-4-[2-(trans-4-ethynylcyclohexyl)ethyl]benzene, 1-butyloxy-4-[2-(trans-4-ethynylcyclohexyl)ethyl]benzene, 1-pentyloxy-4-[2-(trans-4-ethynylcyclohexyl)ethyl]benzene, 1-hexyloxy-4-[2-(trans-4-ethynylcyclohexyl)ethyl]benzene.

EXAMPLE 15

A solution of 750 mg of trans-1-ethynyl-4-[2-(trans-4-pentylcyclohexyl)ethyl]cyclohexane (prepared according to Example 14) in 75 ml of a 4:1 mixture of absolute tetrahydrofuran and hexamethylphosphoric acid triamide was placed at −45° C. in a sulphonation flask under argon gasification and treated within 2 minutes with 3.3 ml of a 1.0N solution of butyl lithium in hexane. The mixture was subsequently stirred at −20° C. for a further 1 hour, then cooled to −78° C. and treated with 490 μl of phenyl cyanate in a single portion. The mixture was then stirred at −78° C. for a further 2.5 hours, poured into 200 ml of water and extracted three times with 150 ml of diethyl ether each time. The organic phases were washed twice with 150 ml of water each time and once with 100 ml of saturated sodium chloride solution, dried over magnesium sulphate and concentrated. Low-pressure chromatography (0.5 bar) of the residue (2.6 g) on silica gel with hexane gave in sequence 194 mg (25.8%) of trans-1-ethynyl-4-[2-(trans-4-pentylcyclohexyl)ethyl]cyclohexane and 284 mg (34.8%) of trans-4-[2-(trans-4-pentylcyclohexyl)ethyl]cyclohexanepropiolonitrile (purity 98.9%). A recrystallization of the nitrile from methanol yielded colourless crystals (purity 99.4%); m.p. (C-N) 51.4% and cl.p. (N-I) 112.7° C.

The following compounds can be manufactured in an analogous manner:

Trans-4-[2-(trans-4-propylcyclohexyl)ethyl]cyclohexanepropiolonitrile, trans-4-[2-(trans-4-butylcyclohexyl)ethyl]cyclohexanepropiolonitrile, trans-4-[2-(trans-4-hexylcyclohexyl)ethyl]cyclohexanepropiolonitrile, trans-4-[2-(trans-4-heptylcyclohexyl)ethyl]cyclohexanepropiolonitrile, trans-4-[2-(p-propylphenyl)ethyl]cyclohexanepropiolonitrile, trans-4-[2-(p-butylphenyl)ethyl]cyclohexanepropiolonitrile, trans-4-[2-(p-pentylphenyl)ethyl]cyclohexanepropiolonitrile, trans-4-[2-(p-hexylphenyl)ethyl]cyclohexanepropiolonitrile, trans-4-[2-(p-heptylphenyl)ethyl]cyclohexanepropiolonitrile, trans-4-[2-(p-ethoxyphenyl)ethyl]cyclohexanepropiolonitrile, trans-4-[2-(p-propyloxyphenyl)ethyl]cyclohexanepropiolonitrile, trans-4-[2-(p-butyloxyphenyl)ethyl]cyclohexanepropiolonitrile, trans-4-[2-(p-pentyloxyphenyl)ethyl]cyclohexanepropiolonitrile, trans-4-[2-(p-hexyloxyphenyl)ethyl]cyclohexanepropiolonitrile.

EXAMPLE 16

A solution of 2.55 g of 1-ethynyl-4-(trans-4-pentylcyclohexyl)benzene (prepared according to Example 3) in 90 ml of absolute tetrahydrofuran was placed at −20° C. in a sulphonation flask under argon gasification and treated within 5 minutes with 11.0 ml of a 1.0N solution of butyl lithium in hexane. The clear yellow mixture was subsequently stirred at −20° C. for a further 30 minutes and then treated in sequence with 10 ml of hexamethylphosphoric acid triamide and 747 μl of methyl iodide. After warming to room temperature, the now dark violet mixture was stirred for a further 4 hours, subsequently poured into 150 ml of water and extracted three times with 150 ml of petroleum ether each time. The organic phases were washed twice with 200 ml of water each time, dried over magnesium sulphate and concentrated. Low-pressure chromatography (0.5 bar) of the residue (3.01 g) on silica gel with hexane gave in sequence 806 mg (31.7%) of 1-ethynyl-4-(trans-4-pentylcyclohexyl)benzene, 431 mg (16.3%) of a mixture of 1-ethynyl-4-(trans-4-pentylcyclohexyl)benzene and 1-(1-propynyl)-4-(trans-4-pentylcyclohexyl)benzene and 601 mg (22.4%) of 1-(1-propynyl)-4-(trans-4-pentylcyclohexyl)benzene. A recrystallization of the last fraction from 50 ml of methanol yielded 464 mg of 1-(1-propynyl)-4-(trans-4-pentylcyclohexyl)benzene as colourless crystals; m.p. (C-N) 41.6° C., cl.p. (N-I) 64.9° C.; $\eta(22°$ C.$)=23$ cp: $\eta(45°$ C.$)=7.7$ cp.

The following compounds can be manufactured in an analogous manner:

1-(1-Propynyl)-4-(trans-4-propylcyclohexyl)benzene, m.p. (C-N) 45.1° C., cl.p. (N-I) 53.7° C.,
1-(1-propynyl)-4-(trans-4-butylcyclohexyl)benzene,
1-(1-propynyl)-4-(trans-4-hexylcyclohexyl)benzene,
1-(1-propynyl)-4-(trans-4-heptylcyclohexyl)benzene, m.p. (C-N) 43.5° C., cl.p. (N-I) 66.8° C.,
1-(1-butynyl)-4-(trans-4-propylcyclohexyl)benzene,
1-(1-butynyl)-4-(trans-4-butylcyclohexyl)benzene,
1-(1-butynyl)-4-(trans-4-pentylcyclohexyl)benzene, m.p. (C-N) 29.5° C., cl.p. (N-I) 31.4° C.,
1-(1-butynyl)-4-(trans-4-hexylcyclohexyl)benzene,
1-(1-butynyl)-4-(trans-4-heptylcyclohexyl)benzene,
1-(1-pentynyl)-4-(trans-4-propylcyclohexyl)benzene,
1-(1-pentynyl)-4-(trans-4-butylcyclohexyl)benzene,
1-(1-pentynyl)-4-(trans-4-pentylcyclohexyl)benzene, m.p. (C-N) 20.0° C., cl.p. (N-I) 31.3° C.,
1-(1-pentynyl)-4-(trans-4-hexylcyclohexyl)benzene,
1-(1-pentynyl)-4-(trans-4-heptylcyclohexyl)benzene,
4-(1-propynyl)-4'-pentylbiphenyl, m.p. (C-S) 60.5° C., cl.p. (S-I) 83.4° C.,
1-(1-propynyl)-4-[2-(trans-4-butylcyclohexyl)ethyl]benzene, m.p. (C-N) 33.1° C., cl.p. (N-I) 38.6° C.,
1-(1-propynyl)-4-[2-(trans-4-pentylcyclohexyl)ethyl]benzene, m.p. (C-N) 46.8° C., cl.p. (N-I) 55.3° C., $\eta(22°$ C.$)=18$ cp,
1-(1-propynyl)-4-[2-(trans-4-heptylcyclohexyl)ethyl]benzene, m.p. (C-N) 44.4° C., cl.p. (N-I) 58.0° C.,
1-(1-butynyl)-4-[2-(trans-4-butylcyclohexyl)ethyl]benzene, m.p. (C-N) 6.1° C., cl.p. (N-I) 9.5° C.,
1-(1-pentynyl)-4-[2-(trans-4-butylcyclohexyl)ethyl]benzene, m.p. 14.3° C., cl.p. 22.6° C.,
1-[2-[trans-4-(1-pentynyl)cyclohexyl]ethyl]-4-butyloxybenzene, m.p. (C-S) 21.6° C., cl.p. (S-I) 25.3° C.

EXAMPLE 17

A solution of 1.42 g of β,β-dibromo-p-[2-(trans-4-pentylcyclohexyl)ethyl]styrene (prepared according to Example 5) in 32 ml of absolute tetrahydrofuran was placed at about 31 45° C. in a sulphonation flask under argon gasification and treated within 5 minutes with 8.0 ml of a 1.2N solution of butyl lithium in hexane. After completed addition, the reaction mixture was stirred at this temperature for a further 90 minutes, before it was treated at −40° C. in sequence with 3.2 ml of hexamethylphosphoric acid triamide and 0.62 ml of butyl iodide. After warming to room temperature, the mixture was stirred for a further 24 hours, subsequently poured into 50 ml of water and extracted three times with 50 ml of petroleum ether each time. The organic phases were washed a further twice with 50 ml of water each time and once with 50 ml of saturated sodium chloride solution, dried over magnesium sulphate and concentrated. Low-pressure chromatography (0.5 bar) of the residue (1.07 g) on silica gel with hexane as the eluant gave 840 mg (81%) of 1-(1-pentynyl)-4-[2-(trans-4-pentylcyclohexyl)ethyl]benzene as colourless crystals (purity according to gas chromatography 98.3%). Recrystallization from 75 ml of methanol yielded 634 mg of 1-(1-pentynyl)-4-[2-(trans-4-pentylcyclohexyl)ethyl]benzene with m.p. (C-I) 37.8° C. and cl.p. (S-I) 30.9° C.

EXAMPLE 18

A solution of 2.87 g of 4-[2-[trans-4-(2,2-dibromovinyl)cyclohexyl]ethyl]-4'-pentylbiphenyl in 100 ml of absolute tetrahydrofuran was placed at −20° C. in a sulphonation flask under argon gasification and treated within 15 minutes with 20.6 ml of a 0.8N solution of butyl lithium in hexane (slight exothermic reaction). The mixture was subsequently stirred for a further 1.5 hours with gradual warming to 0° C., then poured into 100 ml of water and extracted three times with 100 ml of diethyl ether each time. The organic phases were washed a further twice with 100 ml of water each time, dried over magnesium sulphate and concentrated. Low-pressure chromatography (0.5 bar) of the residue (1.98 g) on silica gel with 1% ethyl acetate/petroleum ether as the eluant gave 1.94 g (98%) of 4-[2-(trans-4-ethynylcyclohexyl)ethyl]-4'-pentylbiphenyl. Two-fold recrystallization from ethanol and repeated low-pressure chromatography (0.5 bar) of the crystallizate on silica gel with hexane as the eluant finally yielded 732 mg of mixed fractions and 684 mg of pure 4-(2-(trans-4-ethynylcyclohexyl)ethyl]-4'-pentylbiphenyl with m.p. (C-S) 66.0° C., t.p. (S-S) 107° C., t.p. (S-N) 115.5° C. and cl.p. (N-I) 126.4° C.

The 4-[2-[trans-4-(2,2-dibromovinyl)cyclohexyl]ethyl]-4'-pentylbiphenyl used as the starting material was prepared as follows:

(a) A solution of 10 g of 4-cyano-4'-pentylbiphenyl in 150 ml of methylene chloride was placed at −78° C. in a sulphonation flask under argon gasification and treated within 15 minutes with 54 ml of a 1.5N solution of diisobutylaluminium hydride in toluene. Subsequently, the mixture was stirred at −78° C. for a further 30 minutes, then poured cautiously into 50 ml of 2N hydrochloric acid and extracted three times with 100 ml of methylene chloride each time. The organic phases were washed a further twice with 100 ml of water each time, dried over magnesium sulphate and concentrated. Low-pressure chromatography (0.5 bar) of the oily residue (22.0 g) on silica gel with 3% ethyl acetate/petroleum ether gave 10.0 g (99%) of 4'-pentyl-4-biphenylylcarboxaldehyde as a colourless viscous oil (purity 98%).

(b) 1.5 g of lithium aluminium hydride were suspended in 150 ml of absolute tetrahydrofuran in a sulphonation flask under argon gasification, treated within 15 minutes at room temperature with a solution of 10.0 g of 4′-pentyl-4-biphenylylcarboxaldehyde in 20 ml of absolute tetrahydrofuran and subsequently stirred at room temperature for 1 hour. Then, the reaction mixture was quenched with 50 ml of 2N hydrochloric acid and extracted three times with 100 ml of diethyl ether each time. The organic phases were washed twice with 50 ml of water each time, dried over magnesium sulphate and concentrated. There were obtained 9.4 g (93%) of 4-(hydroxymethyl)-4′-pentylbiphenyl as a colourless, crystallizing oil (purity 98.2%) which was used without additional purification.

(c) A solution of 9.4 g of 4-(hydroxymethyl)-4′-pentylbiphenyl in 150 ml of methylene chloride was placed at 0° C. in a sulphonation flask under argon gasification and treated within 5 minutes with 3.4 ml of a 62% aqueous hydrogen bromide solution. The mixture was subsequently stirred at room temperature for a further 15 hours, then poured into 50 ml of 5% sodium hydrogen carbonate solution and extracted three times with 100 ml of methylene chloride each time. The organic phases were washed twice with 100 ml of water each time, dried over magnesium sulphate and concentrated. Low-pressure chromatography (0.5 bar) of the residue (10.8 g) on silica gel with 5% ethyl acetate/petroleum as the eluant gave 7.5 g (64%) of 4-(bromomethyl)-4′-pentylbiphenyl as a colourless oil.

(d) A solution of 11.6 g of triphenylphosphine in 20 ml of ethyl acetate was placed in a sulphonation flask under argon gasification and treated at room temperature within 10 minutes with a solution of 7.5 g of 4-(bromomethyl)-4′-pentylbiphenyl in 15 ml of ethyl acetate. The reaction mixture was subsequently stirred at room temperature for a further 18 hours and then the separated Wittig salt was filtered off, washed with ethyl acetate and dried at 50° C./12 Torr up to constant weight. There were obtained 7.6 g (56%) of (4′-pentyl-4-biphenylyl)methyl-triphenylphosphonium bromide as a colourless powder of melting point 202°–204° C. From the filtrate, concentrated to 50 ml, there could be isolated a further 3.3 g (24%) of the bromide of melting point 202°–204.5° C.

(e) A suspension of 8.7 g of (4′-pentyl-4-biphenylyl)methyl-triphenylphosphonium bromide in 200 ml of t-butyl methyl ether was placed at 0° C. in a sulphonation flask equipped with a thermometer, dropping funnel and solid substance addition tube and treated within 5 minutes with 1.6 g of solid potassium t-butylate. The mixture was subsequently stirred at 0° C. for a further 30 minutes and then a solution of 1.37 g of trans-4-cyanocyclohexanecarboxaldehyde in 30 ml of t-butyl methyl ether was added dropwise thereto. After completion of the addition, the cooling bath was removed and the mixture was stirred for a further 2 hours, before it was poured into 150 ml of water and extracted three times with 150 ml of diethyl ether each time. The organic phases were washed once with 150 ml of water and once with 150 ml of saturated sodium chloride solution, dried over magnesium sulphate and concentrated. The residue (8.06 g) was digested with 300 ml of 10% ethyl acetate/petroleum ether and filtered. Low-pressure chromatography (0.5 bar) of the concentrated filtrate on silica gel with 10% ethyl acetate/petroleum ether gave 2.0 g of colourless crystals of 4-[2-(trans-4-cyanocyclohexyl)ethenyl]-4′-pentylbiphenyl (cis/trans mixture). Digestion of the initially filtered-off triphenylphosphine oxide with 300 ml of 20% ethyl acetate/petroleum ether; filtration and low-pressure chromatography of the concentrated filtrate on silica gel with 20% ethyl acetate/petroleum ether as the eluant yielded a further 1.41 g of product.

(f) 3.4 g of 4-[2-(trans-4-cyanocyclohexyl)ethenyl]-4′-pentylbiphenyl were dissolved in 150 ml of toluene/ethanol (volume ratio 4:1), treated with 300 ml of 10% palladium/carbon and hydrogenated at normal pressure and room temperature until the hydrogen uptake came to a standstill. Filtration of the mixture and low-pressure chromatography (0.5 bar) of the concentrated filtrate on silica gel with 5% ethyl acetate/petroleum ether as the eluant gave 3.08 g of 4-[2-(trans-4-cyanocyclohexyl)-ethyl]-4′-pentylbiphenyl as colourless crystals (purity 99.2%; yield 86% based on trans-4-cyanocyclohexanecarboxaldehyde). By additional recrystallization of a sample from ethanol there was obtained pure product of melting point (C-S) 59.7° C., t.p. (S-S) 68.1° C., t.p. (S-N) 89.0° C. and cl.p. (N-I) 134.5° C.

(g) A solution of 2.6 g of 4-[2-(trans-4-cyanocyclohexyl)ethyl]-4′-pentylbiphenyl in 100 ml of methylene chloride was placed at −78° C. in a sulphonation flask under argon gasification and treated within 5 minutes with 9.5 ml of a 1.5N soution of diisobutylaluminium hydride in toluene. The mixture was subsequently stirred at −78° C. for a further 4.5 hours, then poured into 100 ml of 10% potassium sodium tartrate solution and extracted three times with 100 ml of methylene chloride each time. The organic phases were washed once with 100 ml of 10% potassium sodium tartrate solution, dried over magnesium sulphate and concentrated. Low-pressure chromatography (0.5 bar) of the residue (2.93 g) on silica gel with ethyl acetate as the eluant gave 2.33 g (89%) of trans-4-[2-(4′-pentyl-4-biphenylyl)ethyl]cyclohexanecarboxaldehyde as colourless crystals.

(h) A solution of 6.7 g of triphenylphosphine in 60 ml of methylene chloride was placed at −20° C. under argon gasification in a sulphonation flask equipped with a thermometer, dropping funnel and solid substance addition tube and treated within 5 minutes with 4.3 g of tetrabromomethane. The clear orange solution was stirred at −15° C. for a further 10 minutes and then a solution of 2.33 g of trans-4-[2-(4′-pentyl-4-biphenylyl)ethyl]cyclohexanecarboxaldehyde in 40 ml of methylene chloride was added dropwise at −5° C. within 10 minutes. The mixture was stirred at −5° C. for a further 10 minutes, then poured into 700 ml of hexane and freed from precipitated triphenylphosphine oxide by filtration. The concentrated filtrate was digested with 300 ml of hexane, filtered and concentrated. Low-pressure chromatography (0.5 bar) of the residue (3.5 g) on silica gel with 1% ethyl acetate/petroleum ether gave 2.87 g (87%) of 4-[2-[trans-4-(2,2-dibromovinyl)cyclohexyl]ethyl]-4′-pentylbiphenyl as colourless crystals.

The following compounds were manufactured in an analogous manner:

1-[2-(Trans-4-ethynylcyclohexyl)ethyl]-4-pentylbenzene, m.p. 34.8° C., 1-(2-(trans-4-ethynylcyclohexyl)ethyl]-4-butyloxybenzene, m.p. 39.5° C.

EXAMPLE 19

A solution of 800 mg of 1-[2-(trans-4-ethynylcyclohexyl)ethyl]-4-pentylbenzene (prepared according to Example 18) in 50 ml of diethyl ether was placed at −25° C. in a sulphonation flask under argon gasification and treated within 5 minutes with 3.9 ml of a 0.8N solution of butyl lithium in hexane. After completion of the addition, the mixture was stirred at 0° C. for a further 45 minutes, then cooled to −78° C. and treated within 10 minutes with a solution of 420 μl of phenyl cyanate in 20 ml of absolute diethyl ether. The mixture was stirred at −78° C. for a further 30 minutes, then poured into 100 ml of water and extracted three times with 100 ml of diethyl ether each time. The organic phases were washed twice with 100 ml of water each time and once with 100 ml of saturated sodium chloride solution, dried over magnesium sulphate and concentrated. Low-pressure chromatography (0.5 bar) of the residue (1.13 g) on silica gel with 3% ethyl acetate/petroleum ether gave, in addition to 630 mg of recovered educt, 142 mg of a colourless crystallizing oil which contained 76% of trans-4-[2-(p-pentylphenyl)ethyl]cyclohexanepropiolonitrile in accordance with gas chromatography. Two-fold crystallization from in each case 5 ml of methanol at −20° C. gave 50 mg of pure nitrile; m.p. (C-N) 36.5° C., cl.p. (N-I) 43.0° C.

The following compound was manufactured in an analogous manner:

Trans-4-[2-(p-butyloxyphenyl)ethyl]cyclohexanepropiolonitrile; m.p. (C-N) 66.6° C., cl.p. (N-I) 76.7° C.

EXAMPLE 20

A mixture of 122 mg of trans-4-ethynylcyclohexanecarboxylic acid, 145 mg of trans-4-pentylcyclohexanol, 206 mg of dicyclohexylcarbodiimide and 12.2 mg of 4-(dimethylamino)pyridine in 10 ml of methylene chloride was stirred at room temperature for 21 hours. The separated white precipitate was filtered off, the filtrate was poured into 50 ml of water and extracted three times with 50 ml of methylene chloride each time. The organic phases were washed once with 50 ml of water, twice with 30 ml of 5% aqueous acetic acid each time and twice with 30 ml of water each time, dried over magnesium sulphate and concentrated. Low-pressure chromatography (0.5 bar) of the residue on silica gel with 5% ethyl acetate/petroleum ether gave 159 mg (65%) of trans-4-ethynylcyclohexanecarboxylic acid trans-4-pentylcyclohexyl ester as a colourless crystallizing oil. Additional crystallization from isopropanol at −20° C. yielded and analytically pure ester; m.p. (C-I) 54.2° C., cl.p. (N-I) 40.5° C.

The trans-4-ethynylcyclohexanecarboxylic acid used as the starting material was prepared as follows:

(a) A solution of 24.0 g of tetrabromomethane in 100 ml of methylene chloride was placed at −15° C. in a sulphonation flask under argon gasification and treated within 10 minutes with a solution of 38.0 of triphenylphosphine in 50 ml of methylene chloride. The clear orange solution was stirred at −10° C. for a further 10 minutes and subsequently a solution of 5.0 g of trans-4-cyanocyclohexanecarboxaldehyde in 20 ml of methylene chloride was added dropwise thereto at −5° C. within 10 minutes. The mixture was stirred at 0° C. for a further 30 minutes, then poured into 1 l of 10% ethyl acetate/petroleum ether and freed from precipitated triphenylphosphine oxide by filtration. The concentrated filtrate was again digested with 500 ml of 10% ethyl acetate/petroleum ether, filtered and concentrated. Low-pressure chromatography (0.5 bar) of the residue (14 g) on silica gel with 10% ethyl acetate/petroleum ether gave 11.0 g of trans-4-(2,2-dibromovinyl)-cyclohexanecarbonitrile which was still contaminated with triphenylphosphine. A second low-pressure chromatography of this material on silica gel with 3% ethyl acetate/petroleum ether gave 9.04 g (85%) of pure trans-4-(2,2-dibromovinyl)cyclohexanecarbonitrile, m.p. 77.5°–78.5° C.

(b) A mixture of 1.71 g of trans-4-(2,2-dibromovinyl)-cyclohexanecarbonitrile and 8.14 g of lithium amalgam (1.5%) in 60 ml of absolute tetrahydrofuran was stirred at room temperature for 68 hours in a round flask under argon gasification. The mixture was subsequently filtered. The filtrate was poured into 150 ml of water and extracted three times with 100 ml of diethyl ether each time. The organic phases were washed once with 150 ml of water, dried over magnesium sulphate and concentrated, there being obtained 1.09 g of a crystallizing oil (trans-4-ethynylcyclohexanecarbonitrile).

(c) The crystallizing oil obtained according to paragraph (b) was dissolved in 20 ml of a 10:1 mixture of 2N aqueous potassium hydroxide and ethanol and heated to reflux for 3.25 hours. The cooled mixture was poured into 50 ml of water and extracted twice with 50 ml of diethyl ether each time. The aqueous phase was made acid with 50 ml of 2N sulphuric acid and extracted three times with 100 ml of diethyl ether each time. The organic phases were washed once with 100 ml of saturated sodium chloride solution, dried over magnesium sulphate and concentrated. Additional crystallization from hexane gave pure trans-4-ethynylcyclohexanecarboxylic acid of m.p. 161°–162° C.

The following compound was manufactured in an analogous manner:

Trans-4-ethynylcyclohexanecarboxylic acid p-hexyloxyphenyl ester, m.p. (C-I) 49.8° C., cl.p. (N-I) 34.5° C.

I claim:

1. A compound of the formula

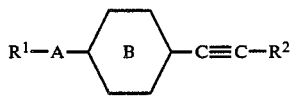

I wherein A together with ring B comprise a central group of the formula:

(a) 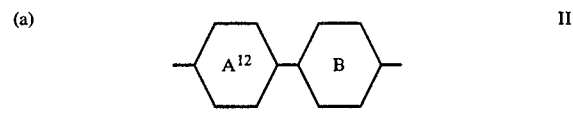

II wherein ring $A^{12}$ is trans-1,4-disubstituted cyclohexane, trans-2,5-disubstituted 1,3-dioxane linked in the 2-position with ring B, or when ring B is trans-1,4-disubstituted cyclohexane or $R^2$ is straight-chain alkyl of 1 to 7 carbon atoms, ring $A^{12}$ also can be 1,4-phenylene or 2,5-disubstituted pyrimidine linked in the 2-position with ring B;

(b) 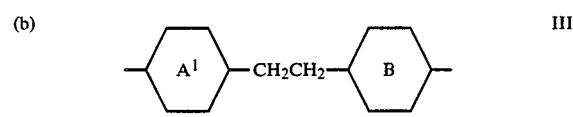

III wherein ring $A^1$ is 1,4-phenylene, or trans-1,4-disubstituted cyclohexane; or (c) 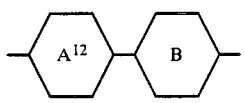 IV wherein ring $A^2$ is 1,4-phenylene or trans-1,4-disubstituted cyclohexane and E is —COO— or —OOC—; ring B is 1,4-phenylene or trans-1,4-disubstituted cyclohexane; $R^1$ is straight-chain alkyl of 1 to 9 carbon atoms or when $R^1$ is attached to a benzene or a pyrimidine ring, $R^1$ also is straight-chain alkoxy of 1 to 9 carbon atoms; and $R^2$ is cyano or straight-chain alkyl of 1 to 7 carbon atoms.

2. A liquid crystalline mixture comprising at least two components, wherein at least one of those components is a compound of the formula:

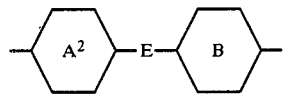 I wherein A together with ring B comprise a central group of the formula:

(a) 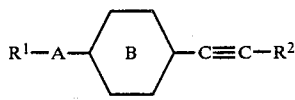 II wherein ring $A^{12}$ is trans-1,4-disubstituted cyclohexane, trans-2,5-disubstituted 1,3-dioxane linked in the 2-position with ring B, or when ring B is trans-1,4-disubstituted cyclohexane or $R^2$ is straight-chain alkyl of 1 to 7 carbon atoms, ring $A^{12}$ also can be 1,4-phenylene or 2,5-disubstituted pyrimidine linked in the 2-position with ring B;

(b) 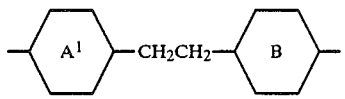 III wherein ring $A^1$ is 1,4-phenylene, or trans-1,4-disubstituted cyclohexane; or (c) 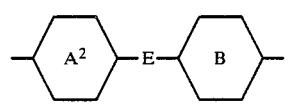 IV wherein ring $A^2$ is 1,4-phenylene or trans-1,4-disubstituted cyclohexane and E is —COO— or —OOC—; ring B is 1,4-phenylene or trans-1,4-disubstituted cyclohexane; $R^1$ is straight-chain alkyl of 1 to 9 carbon atoms or when $R^1$ is attached to a benzene or a pyrimidine ring, $R^1$ also is straight-chain alkoxy of 1 to 9 carbon atoms; and $R^2$ is cyano or straight-chain alkyl of 1 to 7 carbon atoms.

3. An electro-optical cell comprising:
(a) two-plate means;
(b) a liquid crystal disposed between the plate means and including a dielectric of the formula:

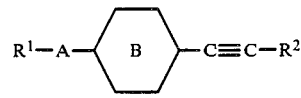 I wherein A together with ring B comprise a central group of the formula:

(i) 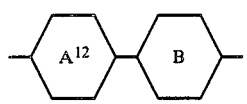 II wherein ring $A^{12}$ is trans-1,4-disubstituted cyclohexane, trans-2,5-disubstituted 1,3-dioxane linked in the 2-position with ring B, or when ring B is trans-1,4-disubstituted cyclohexane or $R^2$ is straight-chain alkyl of 1 to 7 carbon atoms, ring $A^{12}$ also can be 1,4-phenylene or 2,5-disubstituted pyrimidine linked in the 2-position with ring B;

(ii) 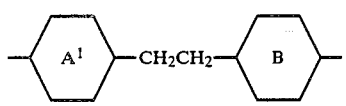 III wherein ring $A^1$ is 1,4-phenylene, or trans-1,4-disubstituted cyclohexane; or (iii) 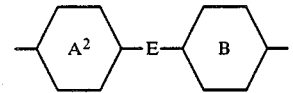 IV wherein ring $A^2$ is 1,4-phenylene or trans-1,4-disubstituted cyclohexane and E is —COO— or —OOC—; ring B is 1,4-phenylene or trans-1,4- disubstituted cyclohexane; $R^1$ is straight-chain alkyl of 1 to 9 carbon atoms or when $R^1$ is attached to a benzene or a pyrimidine ring, $R^1$ also is straight-chain alkoxy of 1 to 9 carbon atoms; and $R^2$ is cyano or straight-chain alkyl of 1 to 7 carbon atoms.

4. The compound of claim 1 wherein A together with ring B is a central group of formula II in which ring $A^{12}$ is trans-1,4-disubstituted cyclohexane, trans-2,5-disubstituted 1,3-dioxane linked in the 2-position with ring B or when ring B is trans-1,4-disubstituted cyclohexane or $R^2$ is alkyl, ring $A^{12}$ also is 1,4-phenylene or 2,5-disubstituted pyrimidine linked in the 2-position with ring B.

5. The compound of claim 1 wherein A together with ring B is a central group of formula III in which ring $A^1$ is 1,4-phenylene or trans-1,4-disubstituted cyclohexane.

6. The compound of claim 1 wherein A together with ring B is a central group of formula IV in which ring $A^2$ is 1,4-phenylene or trans-1,4-disubstituted cyclohexane and E is an ester group.

7. The compound of claim 1 wherein ring B is saturated.

8. The compound of claim 1 having the formula

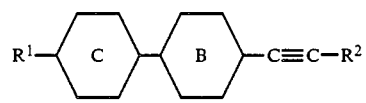 XX

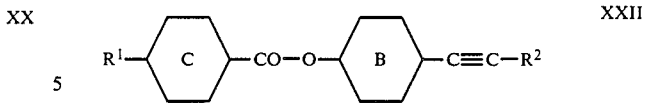 XXII wherein each of rings B and C is 1,4-phenylene or trans-1,4-disubstituted cyclohexane; R¹ is straight-chain alkyl of 1 to 9 carbon atoms or when R¹ is attached to a benzene ring, R¹ also is straight-chain alkoxy of 1 to 9 carbon atoms; and R² is straight-chain alkyl of 1 to 7 carbon atoms or, when at least one of rings B and C is trans-1,4-disubstituted cyclohexane, R² also is cyano.

9. The compound of claim 8 wherein one of rings B and C is trans-1,4-disubstituted cyclohexane and the other is 1,4-phenylene.

10. The compound of claim 8 wherein ring B is saturated.

11. The compound of claim 1 wherein R² is cyano, methyl, ethyl or propyl.

12. The compound of claim 11 wherein R² is cyano or methyl.

13. The compound of claim 1 wherein R¹ is straight-chain alkyl of 3 to 7 carbon atoms or when R¹ is attached to a benzene or pyrimidine ring, R¹ also is straight-chain alkoxy of 2 to 6 carbon atoms.

14. The compound of claim 12 wherein R¹ is straight-chain alkyl of 3 to 7 carbon atoms or when R¹ is attached to a benzene, or pyrimidine ring, R¹ also is straight-chain alkoxy of 2 to 6 carbon atoms.

15. The compound of claim 1 having the formula

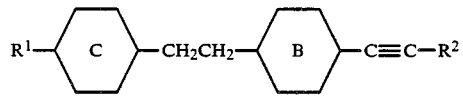 XXI wherein ring C is 1,4-phenylene or trans-1,4-disubstituted cyclohexane; ring B is 1,4-phenylene or trans-1,4-disubstituted cyclohexane; R¹ is straight-chain alkyl of 1 to 9 carbon atoms or when R¹ is attached to a benzene ring, R¹ also is straight-chain alkoxy of 1 to 9 carbon atoms; and R² is cyano or straight-chain alkyl of 1 to 7 carbon atoms.

16. The compound of claim 15 wherein at least one of rings B and C is trans-1,4-disubstituted cyclohexane.

17. The compound of claim 15 wherein ring B is saturated.

18. The compound of claim 15 wherein R² is cyano, methyl, ethyl or propyl.

19. The compound of claim 18 wherein R² is cyano or methyl.

20. The compound of claim 15 wherein R¹ is straight-chain alkyl of 3 to 7 carbon atoms or when R¹ is attached to a benzene ring, R¹ also is straight-chain alkoxy of 2 to 6 carbon atoms.

21. The compound of claim 19 wherein R¹ is straight-chain alkyl of 3 to 7 carbon atoms or when R¹ is attached to a benzene ring, R¹ also is straight-chain alkoxy of 2 to 6 carbon atoms.

22. The compound of claim 1 having the formula wherein ring C is 1,4-phenylene or trans-1,4-disubstituted cyclohexane; ring B is 1,4-phenylene or trans-1,4-disubstituted cyclohexane; R¹ is straight-chain alkyl of 1 to 9 carbon atoms or when R¹ is attached to a benzene ring, R¹ also is straight-chain alkoxy of 1 to 9 carbon atoms; and R² is cyano or straight-chain alkyl of 1 to 7 carbon atoms.

23. The compound of claim 22 wherein ring B is 1,4-phenylene.

24. The compound of claim 22 wherein ring B is saturated.

25. The compound of claim 22 wherein R² is cyano, methyl, ethyl or propyl.

26. The compound of claim 25 wherein R² is cyano or methyl.

27. The compound of claim 22 wherein R¹ is straight-chain alkyl of 3 to 7 carbon atoms or when R¹ is attached to a benzene ring, R¹ also is straight-chain alkoxy of 2 to 6 carbon atoms.

28. The compound of claim 26 wherein R¹ is straight-chain alkyl of 3 to 7 carbon atoms or when R¹ is attached to a benzene ring, R¹ also is straight-chain alkoxy of 2 to 6 carbon atoms.

29. The compound of claim 1 having the formula

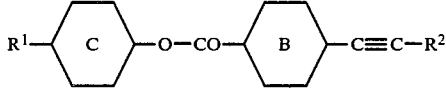 XXIII wherein ring C is 1,4-phenylene or trans-1,4-disubstituted cyclohexane; ring B is 1,4-phenylene or trans-1,4-disubstituted cyclohexane; R¹ is straight-chain alkyl of 1 to 9 carbon atoms or when R¹ is attached to a benzene ring, R¹ also is straight-chain alkoxy of 1 to 9 carbon atoms; and R² is cyano or straight-chain alkyl of 1 to 7 carbon atoms.

30. The compound of claim 29 wherein ring B is saturated.

31. The compound of claim 29 wherein R² is cyano, methyl, ethyl or propyl.

32. The compound of claim 31 wherein R² is cyano or methyl.

33. The compound of claim 29 wherein R¹ is straight-chain alkyl of 3 to 7 carbon atoms or when R¹ is attached to a benzene ring, R¹ also is straight-chain alkoxy of 2 to 6 carbon atoms.

34. The compound of claim 32 wherein R¹ is straight-chain alkyl of 3 to 7 carbon atoms or when R¹ is attached to a benzene ring, R¹ also is straight-chain alkoxy of 2 to 6 carbon atoms.

35. The compound of claim 29 wherein ring B is 1,4-phenylene.

36. The compound of claim 1 having the formula

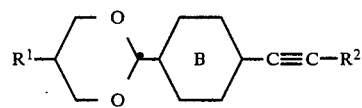 XXIV wherein ring B is 1,4-phenylene or trans-1,4-disubstituted cyclohexane; $R^1$ is straight-chain alkyl of 1 to 9 carbon atoms and $R^2$ is cyano or straight-chain alkyl of 1 to 7 carbon atoms.

37. The compound of claim 36 wherein ring B is saturated.

38. The compound of claim 36 wherein $R^2$ is cyano, methyl, ethyl or propyl.

39. The compound of claim 38 wherein $R^2$ is cyano or methyl.

40. The compound of claim 36 wherein $R^1$ is straight-chain alkyl of 3 to 7.

41. The compound of claim 39 wherein $R^1$ is straight-chain alkyl of 3 to 7.

42. The compound of claim 1 having the formula

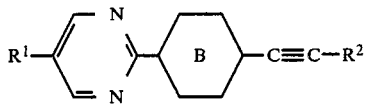

XXV wherein ring B is 1,4-phenylene or trans-1,4-disubstituted cyclohexane; $R^1$ is straight-chain alkyl of 1 to 9 carbon atoms or straight-chain alkoxy of 1 to 9 carbon atoms; and $R^2$ is straight-chain alkyl of 1 to 7 carbon atoms or, when ring B is trans-1,4-disubstituted cyclohexane, $R^2$ also is cyano.

43. The compound of claim 42 wherein ring B is saturated.

44. The compound of claim 42 wherein $R^2$ is cyano, methyl, ethyl or propyl.

45. The compound of claim 44 wherein $R^2$ is cyano or methyl.

46. The compound of claim 42 wherein $R^1$ is straight-chain alkyl of 3 to 7 carbon atoms or straight-chain alkoxy of 2 to 6 carbon atoms.

47. The compound of claim 45 wherein $R^1$ is straight-chain alkyl of 3 to 7 carbon atoms or straight-chain alkoxy of 2 to 6 carbon atoms.

48. The compound of claim 1 wherein ring B is aromatic.

49. The compound of claim 48 wherein $R^2$ is straight-chain alkyl of 1 to 7 carbon atoms.

50. The compound of claim 8 wherein $R^2$ is cyano, methyl, ethyl or propyl.

51. The compound of claim 50 wherein $R^2$ is cyano or methyl.

52. The compound of claim 8 wherein $R^1$ is straight-chain alkyl of 3 to 7 carbon atoms or when $R^1$ is attached to a benzene ring, $R^1$ also is straight-chain alkoxy of 2 to 6 carbon atoms.

53. The compound of claim 51 wherein $R^1$ is straight-chain alkyl of 3 to 7 carbon atoms or when $R^1$ is attached to a benzene ring, $R^1$ also is straight-chain alkoxy of 2 to 6 carbon atoms.

54. The compound of claim 1, p-(trans-4-pentylcyclohexyl)phenylpropiolonitrile.

55. The compound of claim 1, p-[2-(trans-4-pentylcyclohexyl)ethyl]phenylpropiolonitrile.

56. The compound of claim 1, p-(trans-5-pentyl-1,3-dioxan-2-yl)phenylpropiolonitrile.

57. The compound of claim 1, p-(trans-5-butyl-1,3-dioxan-2-yl)phenylpropiolonitrile.

58. The compound of claim 1, trans-4-pentylcyclohexanecarboxylic acid p-(2-cyanoethynyl)phenyl ester.

59. The compound of claim 1, trans-4-[2-(trans-4-pentylcyclohexyl)ethyl]cyclohexanepropiolonitrile.

60. The compound of claim 1, 1-(1-propynyl)-4-(trans-4-propylcyclohexyl)benzene.

61. The compound of claim 1, 1-(1-propynyl)-4-(trans-4-pentylcyclohexyl)benzene.

62. The compound of claim 1, 1-(1-propynyl)-4-(trans-4-heptylcyclohexyl)benzene.

63. The compound of claim 1, 1-(1-butynyl)-4-(trans-4-pentylcyclohexyl)benzene.

64. The compound of claim 1, 1-(1-pentynyl)-4-(trans-4-pentylcyclohexyl)benzene.

65. The compound of claim 1, 4-(1-propynyl)-4'-pentylbiphenyl.

66. The compound of claim 1, 1-(1-propynyl)-4-[2-(trans-4-butylcyclohexyl)ethyl]benzene.

67. The compound of claim 1, 1-(1-propynyl)-4-[2-(trans-4-pentylcyclohexyl)ethyl]benzene.

68. The compound of claim 1, 1-(1-propynyl)-4-[2-(trans-4-heptylcyclohexyl)ethyl]benzene.

69. The compound of claim 1, trans-4-[2-(p-pentylphenyl)ethyl]cyclohexanepropiolonitrile.

70. The compound of claim 1, trans-4-[2-(p-butyloxyphenyl)ethyl]cyclohexanepropiolonitrile.

* * * * *